United States Patent [19]

Gourlandt

[11] Patent Number: 4,681,565

[45] Date of Patent: Jul. 21, 1987

[54] METHOD AND APPARATUS FOR AUTOMATICALLY TREATING ANIMALS, PREFERABLY BIRDS, SUCH AS YOUNG CHICKS, YOUNG GUINEAFOWLS, YOUNG TURKEYS

[76] Inventor: Albert J. A. Gourlandt, Les Grésillons, 78950 Gambais, France

[21] Appl. No.: 686,246

[22] Filed: Dec. 26, 1984

[30] Foreign Application Priority Data

Dec. 30, 1983 [GB] United Kingdom ................. 8334631

[51] Int. Cl.[4] ................................................ A61M 5/00

[52] U.S. Cl. .................................... 604/115; 604/156; 128/DIG. 1; 119/97 R

[58] Field of Search ............... 119/97, 159; 128/303.1, 128/303.14, DIG. 1; 604/115, 200, 49, 136, 144, 156, 157

[56] References Cited

U.S. PATENT DOCUMENTS

| | | | |
|---|---|---|---|
| 2,051,989 | 8/1936 | Ellis | 17/11 |
| 2,448,421 | 8/1948 | Davis | 17/44.1 |
| 2,731,016 | 1/1956 | Miller | 128/303.1 |
| 2,742,904 | 4/1956 | Lyon | 128/303.1 |
| 2,792,004 | 5/1957 | Sandy | 128/303.1 |
| 2,945,496 | 7/1960 | Fosdal | 604/115 |
| 2,952,031 | 9/1960 | Breitkreutz | 17/11 |
| 3,295,524 | 1/1967 | Parker . | |
| 3,302,645 | 2/1967 | Lockmiller | 128/223 |
| 3,434,474 | 3/1969 | Reynolds | 128/253 |
| 3,502,079 | 10/1966 | Simmons et al. . | |
| 3,570,487 | 3/1971 | Reynolds | 128/223 |
| 3,593,714 | 7/1971 | Lyon . | |
| 3,774,578 | 11/1973 | Randolph et al. | 119/97 R |
| 3,964,481 | 6/1976 | Gourlandt et al. . | |
| 3,994,292 | 11/1976 | Goodwin | 128/172 |
| 4,375,814 | 3/1983 | Gourlandt . | |
| 4,446,819 | 5/1984 | Gourlandt | 119/97 R |

FOREIGN PATENT DOCUMENTS

| | | | |
|---|---|---|---|
| 253057 | 7/1964 | Australia | 604/115 |
| 2281060 | 8/1974 | France | 128/303.1 |

*Primary Examiner*—C. Fred Rosenbaum
*Assistant Examiner*—Mario Costantino

[57] ABSTRACT

Apparatus for automatically treating animals such as birds at a high speed. The apparatus includes a frame, a spindle mounted on the frame, drive means for rotating the spindle, and a table mounted on the spindle and provided with a plurality of spaced-apart bird supports capable of supporting birds immobilized in the neck area. A syringe and a suction device are supported on a support means that is freely mounted on the spindle and adapted to move with respect to the frame from a non-operative position to an operative position. The suction device has a nozzle provided with a perforated surface surrounding and extending vertically along the bird's neck area. The suction device serves to draw back an area of the neck skin before an injection is made with the syringe.

5 Claims, 44 Drawing Figures

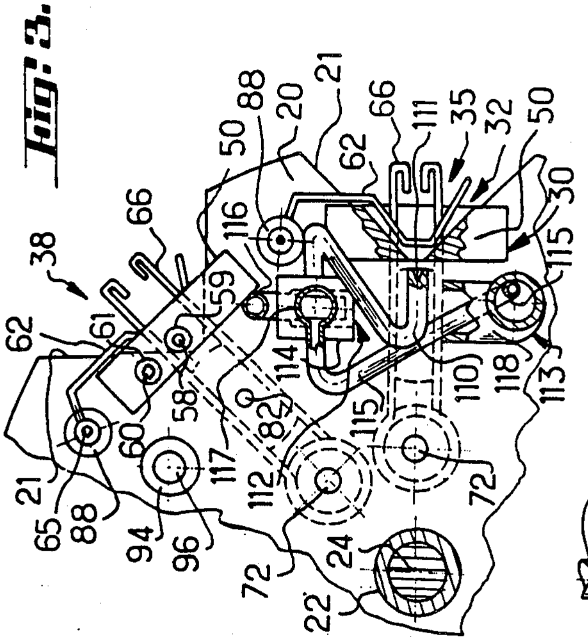
Fig. 3.
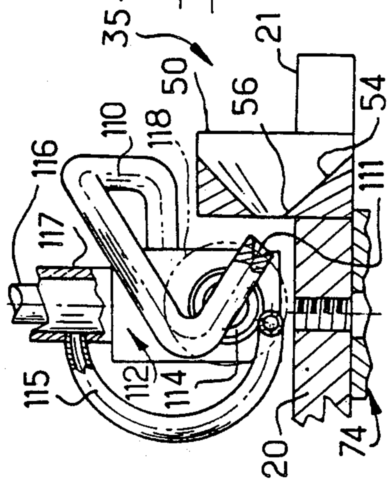
Fig. 9.
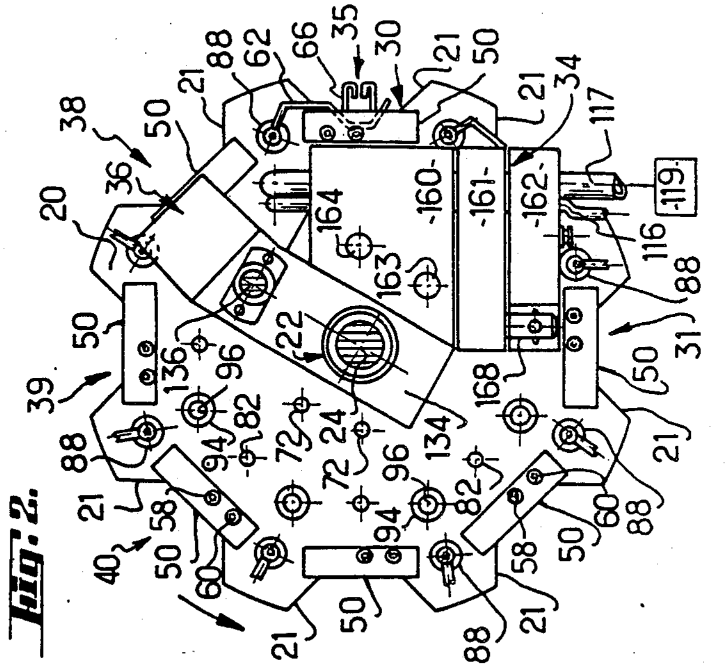
Fig. 2.
Fig. 16.
Fig. 17.

METHOD AND APPARATUS FOR AUTOMATICALLY TREATING ANIMALS, PREFERABLY BIRDS, SUCH AS YOUNG CHICKS, YOUNG GUINEAFOWLS, YOUNG TURKEYS

The invention essentially relates to improvements in a method and apparatus for automatically treating animals, preferbly birds such as young chicks, young guinea-fowls, young turkeys. More specifically, this invention relates to a method and an apparatus for automatically treating animals according to which one can automatically administer a substance to an animal notably a medicine such as an antibiotic, a vaccine or even an aqueous solution or water, and for cauterizing birds.

The inventor of the present invention has already described in U.S. Pat. No. 3,964,881 a device for injecting vaccine into a manually supported chick, using a hypodermic syringe.

On the other hand, the present inventor has also discovered a method and an apparatus for automatically supporting and restraining birds, and preferably young chicks, said method and apparatus in a preferred embodiment being applied for automatically debeaking said birds. This prior inventor's invention is the subject matter of U.S. Pat. No. 4,375,814 granted on Mar. 8, 1983 and its divisional U.S. Pat. No. 4,446,819 granted on May 8, 1984.

The presently claimed invention thus constitutes new and useful improvements to the latter prior applicant's invention and as previously said these improvements allow automatic administration of a substance to an animal notably a medicine such as an antibiotic, vaccine or even water notably by the use of the supporting and restraining device subject matter of the above published U.S. Pat. No. 4,375,814 and its division U.S. Pat. No. 4,446,819.

The present invention offers the same advantages as those subject matter of U.S. Pat. No. 4,375,814 and its division No. 4,446,819 namely by allowing automatic treatment for animals at a very high speed in full safety, the present invention allowing further the automatic administration of a substance to an animal notably a medicine such as an antibiotic, a vaccine or even an aqueous solution or water. The animals are thus alive.

More precisely, according to the present invention the method generally includes providing holding and/or supporting means for holding and/or supporting the animal's head essentially immobilized and treating said held animal, characterized in that it comprises providing a treating assembly in the vicinity of said animal holding and/or supporting means for administering to said animal at least one treating substance such as a liquid and/or a powder or an ointment, notably with healing or calming action, in the vicinity of said substantially immobilized animal's head, said administering assembly being movable between a non-operative position and an operative position.

According to a specific embodiment, this method also comprises injecting one or more treating liquids to said animal.

According into another feature, this method comprises drawing back the neck skin of the held animal and injecting said liquid under said drawn back neck skin subcutaneously.

According to another specific embodiment, the treating assembly comprises administering or applying a powder or an ointment, notably with healing or calming action, essentially onto the beak(s) of a previously debeaked bird.

According to the method of the invention, each treating substance if selected among medicines such as an antibiotic, a vaccine or other biological liquids, for instance vitaminic products, products promoting growth, and/or a powder or an ointment, notably with healing or calming action, and an aqueous solution or water.

According to a further specific feature, the method comprises holding the back of said animal to rearwardly immobilize the animal with respect to the holding and/or supporting means.

On the other hand, the treating assembly can further comprise applying drops, droplets or microdrops; or spraying or atomizing, one or more treating substances at the nose position and/or at least one eye position and/or at the mouth position of the animal (in both cases of applying drops and spraying).

Also, for automatically treating animals at a high speed, the method of the invention is characterized in that at least a part of the holding and/or supporting means is movable according to an endless circuit, a plurality of holding and/or supporting means are provided spaced apart along the endless circuit, said treating assembly being in the vicinity of said endless circuit so that each holding means is caused to pass first at a loading station then at the treating station and thereafter at an unloading station.

The present invention also relates to an apparatus for automatically treating animals having a frame, comprising means for holding and/or supporting the animal's head essentially immobilized and means for treating said held animal, characterized in that said means for treating said held animal comprises an assembly for administering to said animal at least one treating substance such as a liquid and/or powder or an ointment, notably with healing or calming action, in the vicinity, or at least at a location of said substantially immobilized animal's head, said administering assembly being movable between a non-operative position and an operative position with respect to the frame.

Preferably, said administering assembly comprises means for administering to at least one eye, to the nose, to the mouth or other orifice of the animal, one or several drops, droplets or microdrops of said liquid; or for spraying or atomizing said liquid. Also the administering assembly can comprise means for applying a powder or an ointment, notably with healing or calming action essentially on the beak(s) of a debeaked bird.

Advantageously, said drop administering or spraying means comprises at least a substance distributing circuit provided with a treating substance dosage element.

According to a specific feature, said substance administering assembly comprises means for injecting liquid under the skin of said animal, comprising at least a hypodermic syringe.

According to another embodiment, the invention apparatus comprises a suction device for drawing back the neck skin of a held animal, each hypodermic syringe being so mounted as to inject said treating substance under said drawn back neck skin, in operative position (subcutaneous injection).

According to a specific feature, said apparatus comprises a suction breaking element during the period of time where said suction is unnecessary between two successive injecting administering operations.

According to another embodiment, the invention apparatus comprises a safety device preventing the administration of substances when no animal is held in said holding and/or supporting means. According to a specific feature, said safety device comprises a feeling means linked in displacement to the substance administering assembly and a stop means with respect to the feeling means interposing in the path of the feeling means when no animal is held.

Moreover, for automatically treating animals at a high speed, the invention apparatus is further characterized in that at least a part of the holding and/or supporting means is movable according to an endless circuit, a plurality of holding and/or of supporting means being provided spaced apart along said endless circuit so that the holding and/or supporting means is caused to pass first at a loading station then at the treating station and thereafter at an unloading station.

Other characterizing features, purposes or advantages of the present invention will appear as the following non-limitative description proceeds with reference to the appended drawings which refer to the most preferred embodiments for treating animals at a high speed so that an endless circuit is provided but it is understandable from the above that the invention is not limited to the provision of an endless circuit but on the contrary covers any treating apparatus of the type described. In the drawings:

FIG. 2 is a view of the endless circuit, the injection assembly not being shown for a better understanding;

FIG. 3 is a partial top view of the endless circuit showing the debeaking station in the case of the specific treatment of birds;

Figure 1:
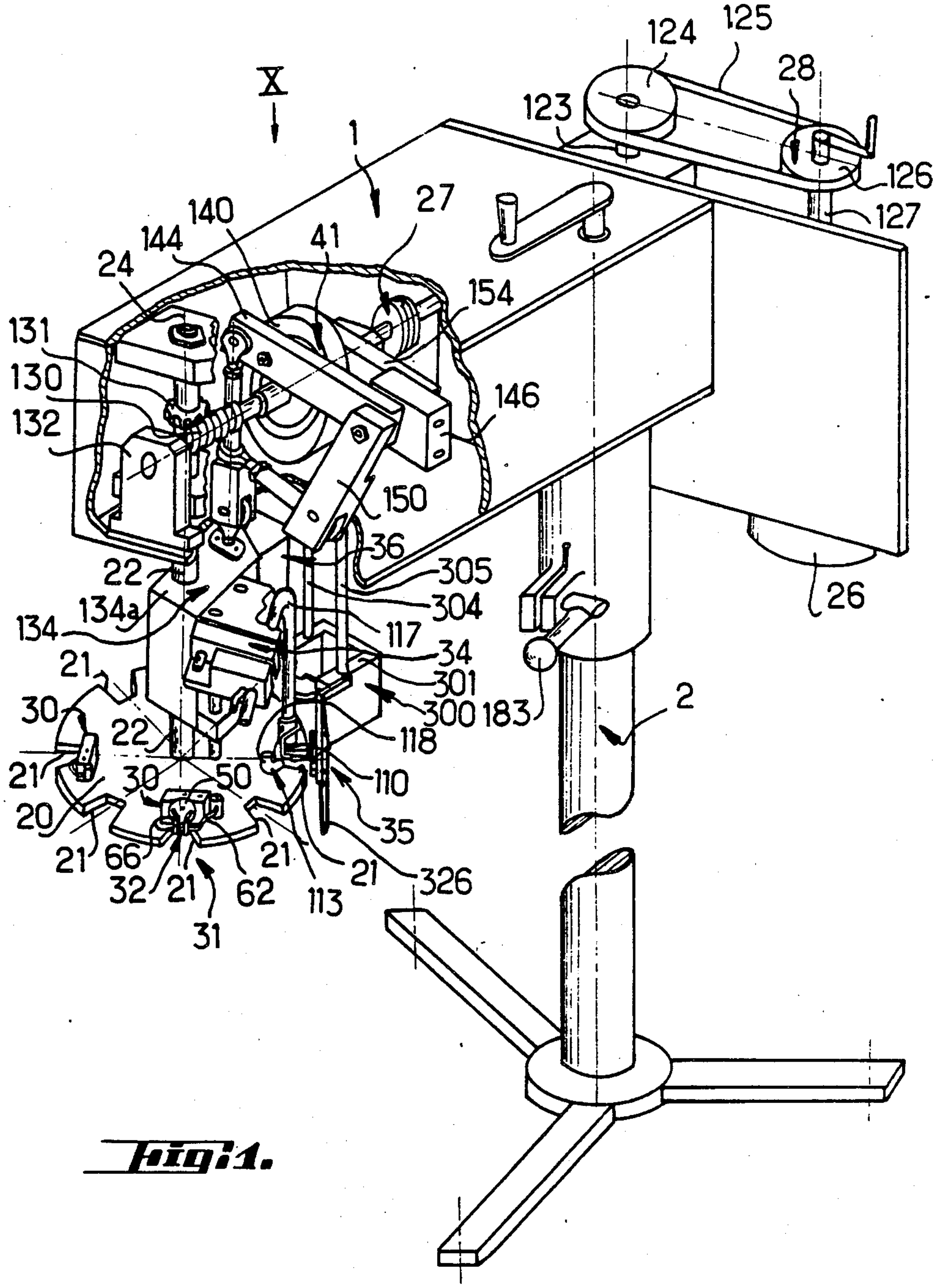
FIG. 1 is a perspective view of an invention apparatus with an endless circuit which is in the example shown constituted by a movable table here rotatively mounted with respect to a frame, some parts of the frame being broken away to show more precisely the drive means for moving the endless circuit and the actuator means for actuating each treating assembly.
Figure 8:
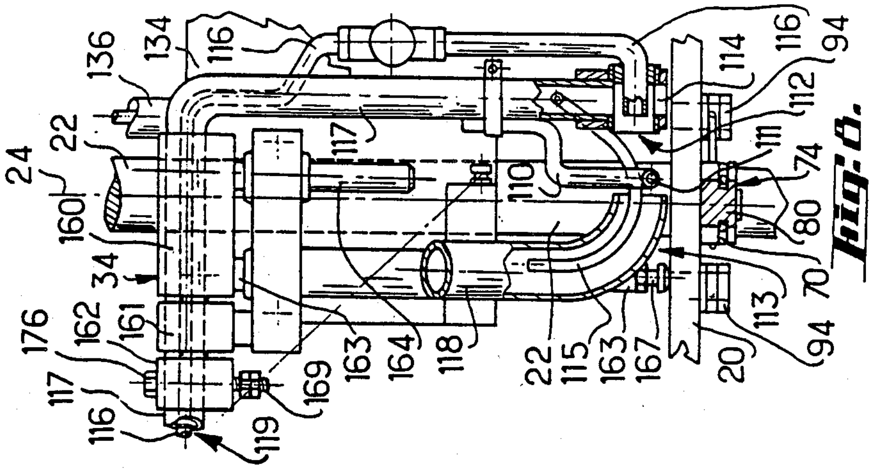
Figure 7:
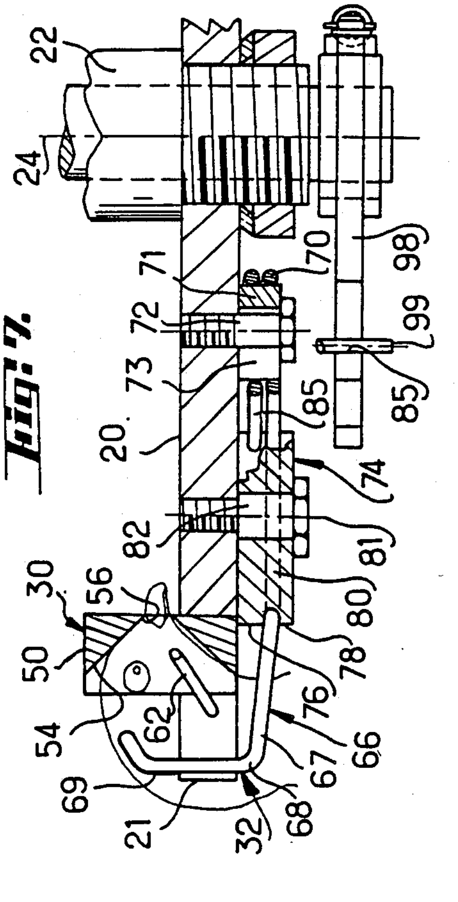
Figure 6A:
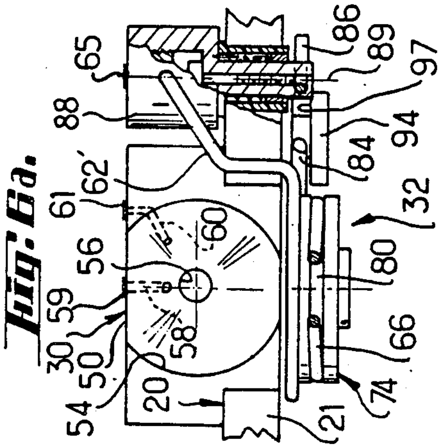
FIG. 6 is a front view of an animal holding means and/or supporting means of the endless circuit.
Figure 6:
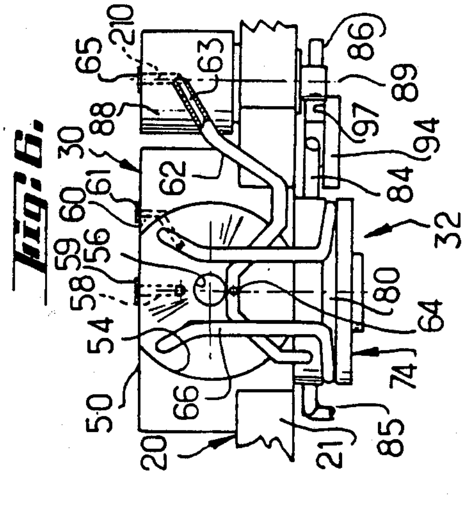
Figure 10:
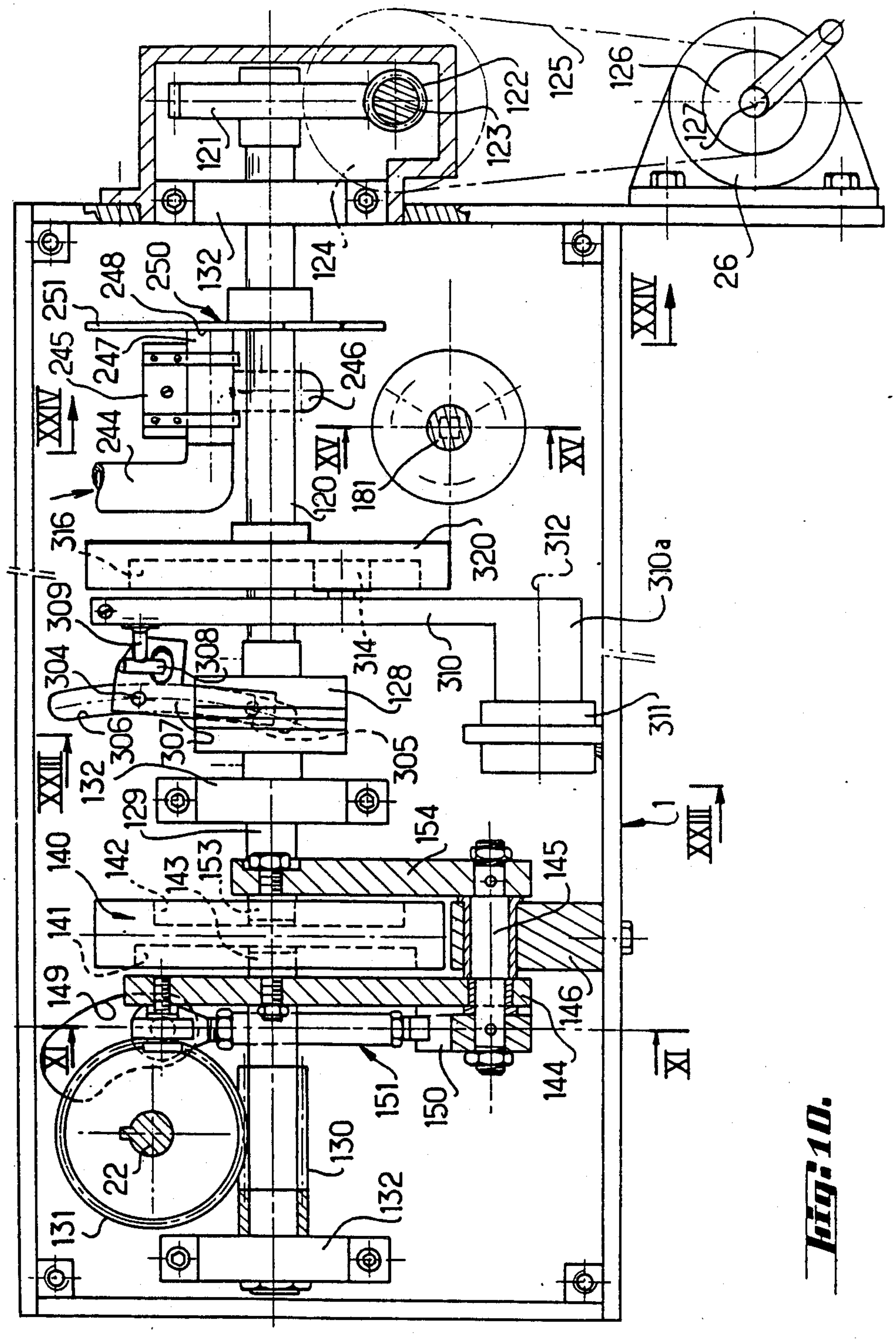
Figure 11:
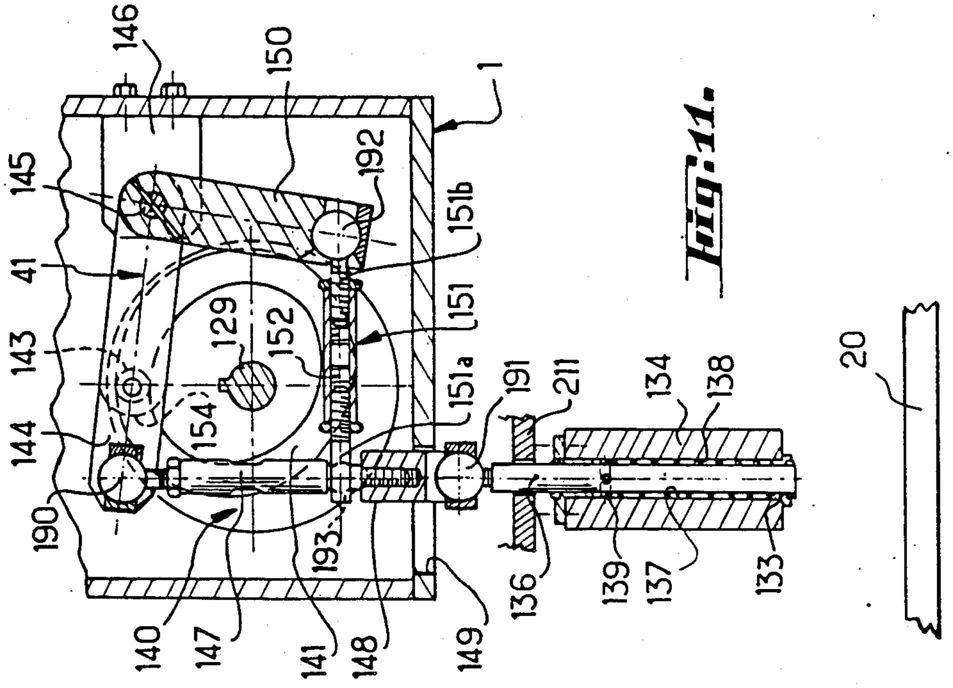
Figure 11A:
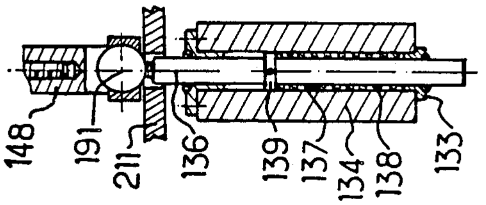
Figure 20A:
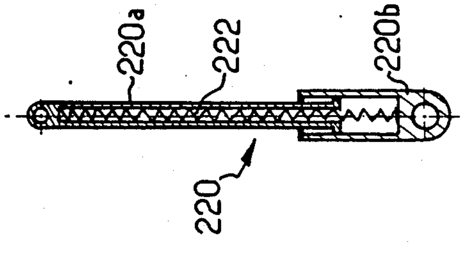
Figure 15:
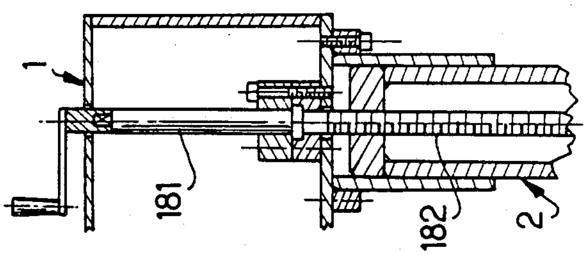
Figure 13:
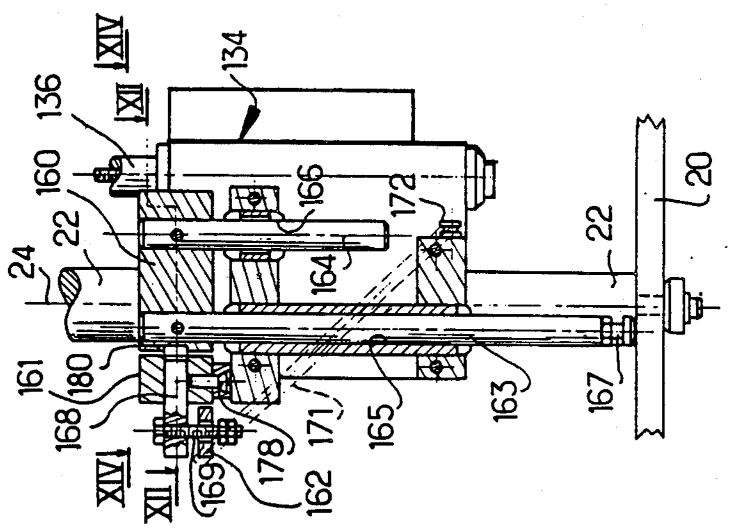
Figure 12:
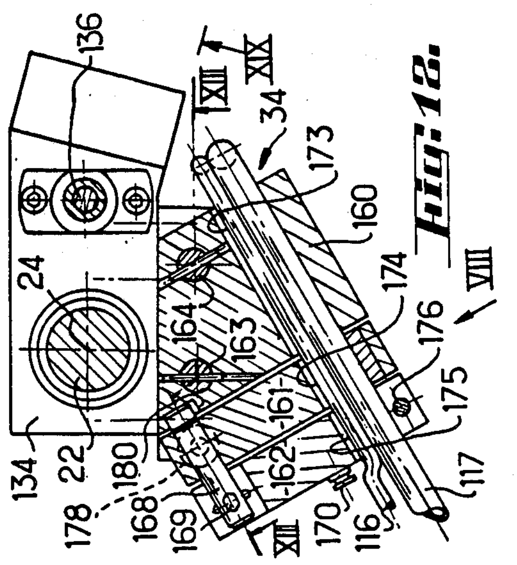
Figure 14:
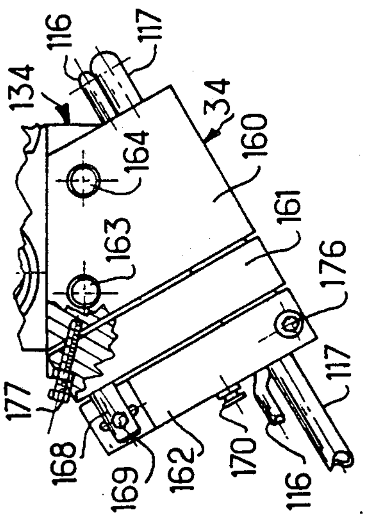
Figure 18B:
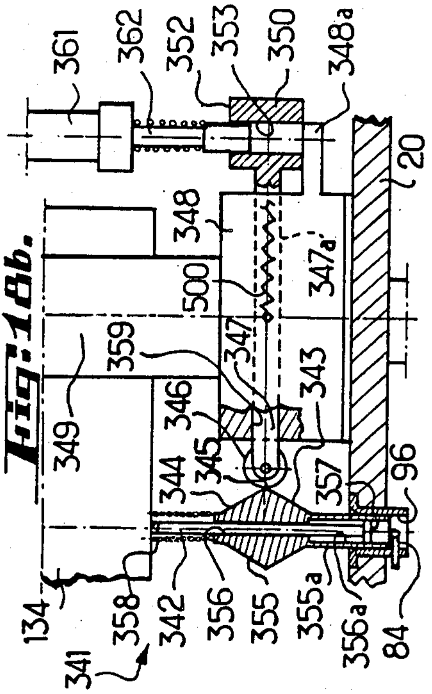
Figure 18A:
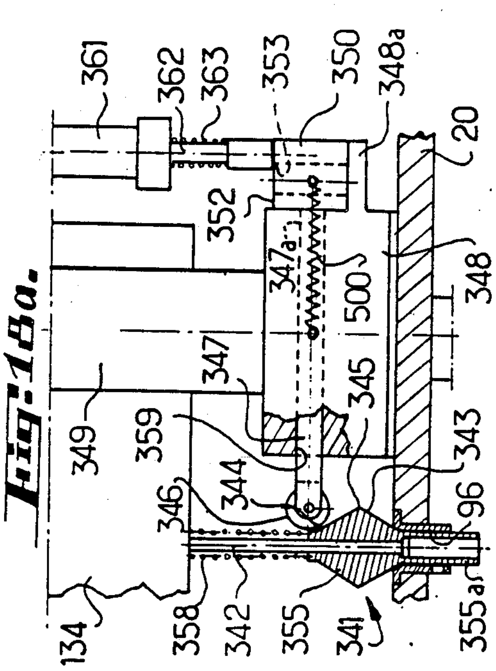
Figure 18:
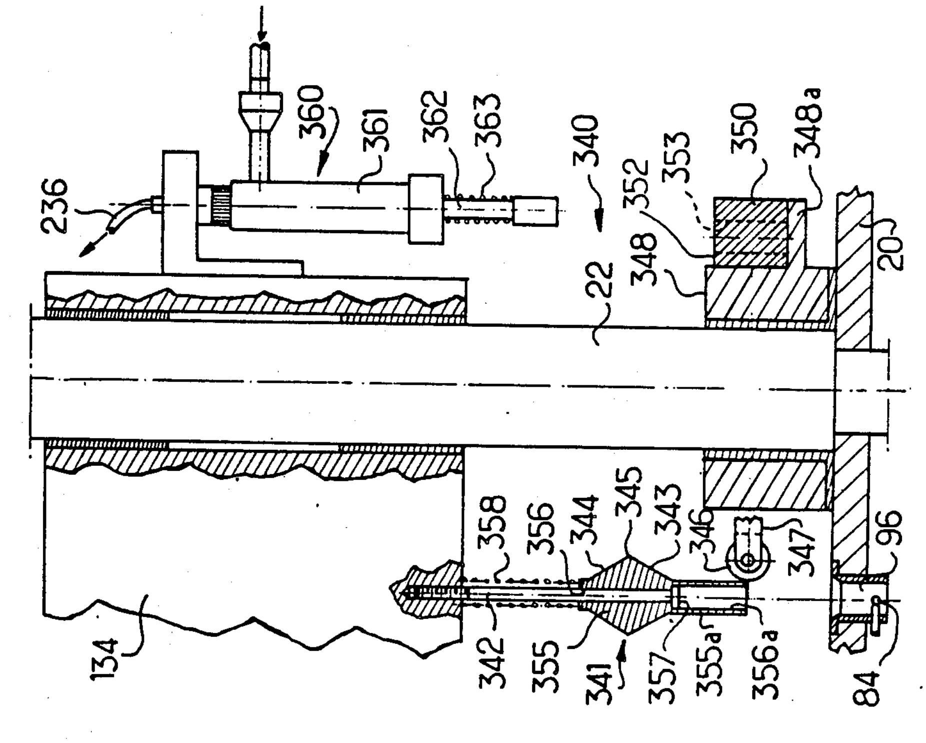
Figure 20:
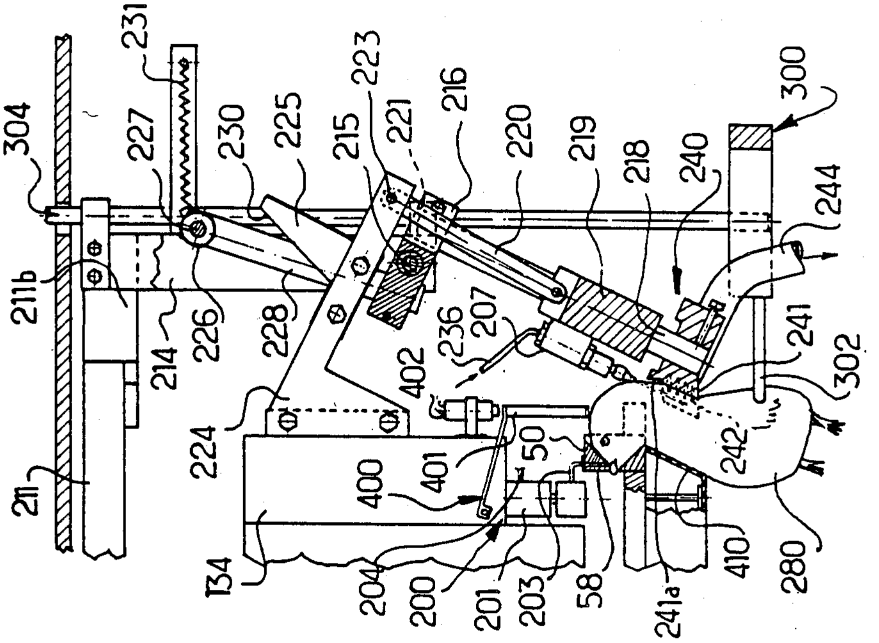
Figure 19:
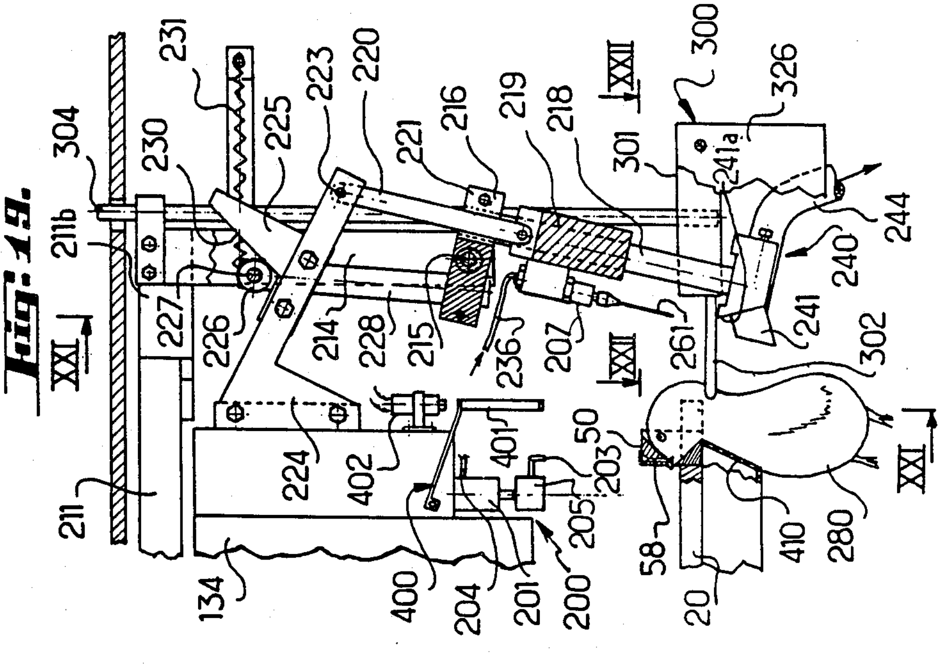
Figure 21:
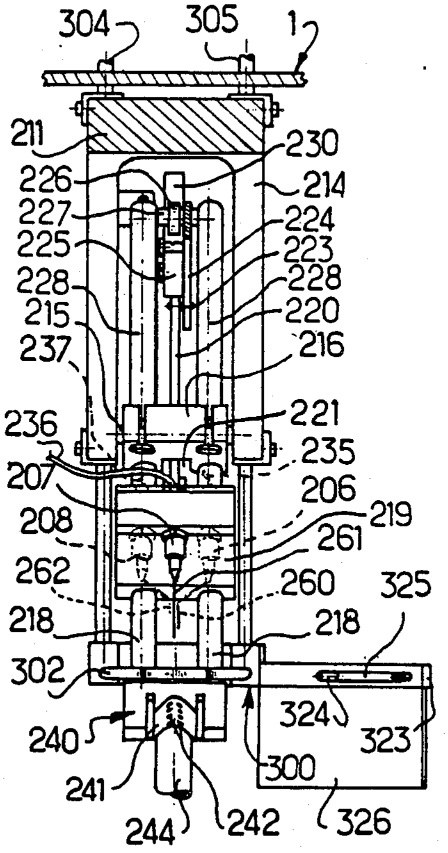
Figure 23:
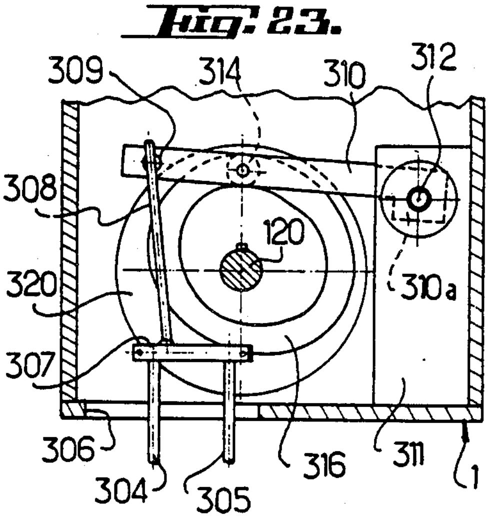
Figure 24:
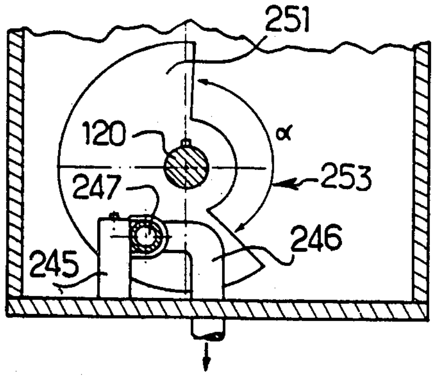
Figure 22:
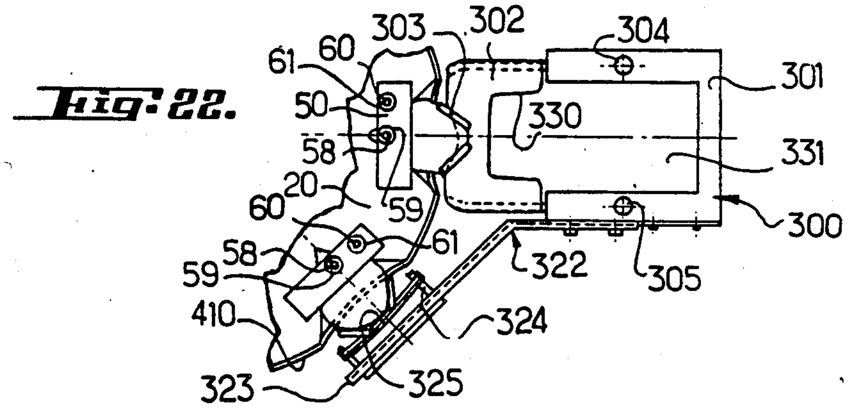
Figure 30:
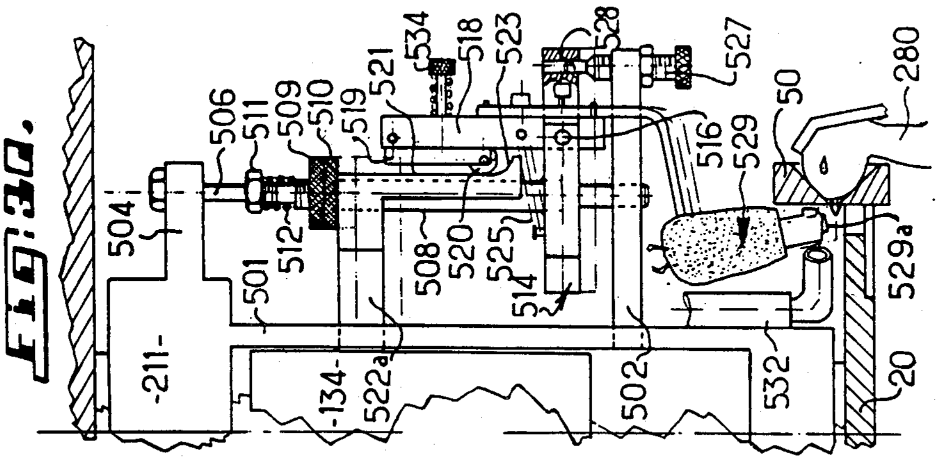
Figure 28:
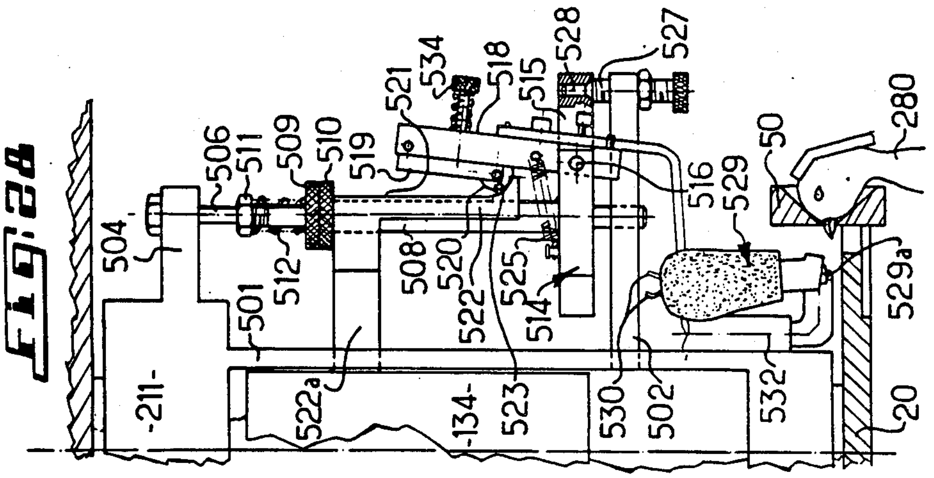
Figure 29:
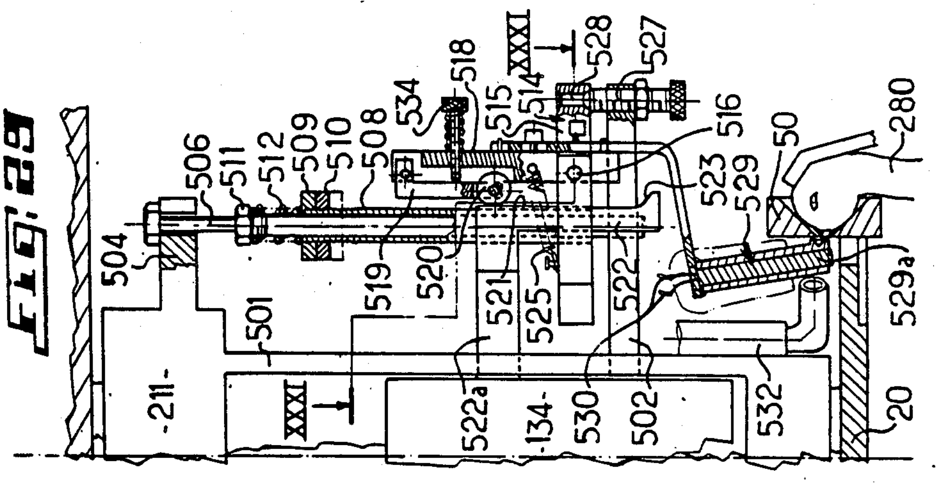
Figure 31:
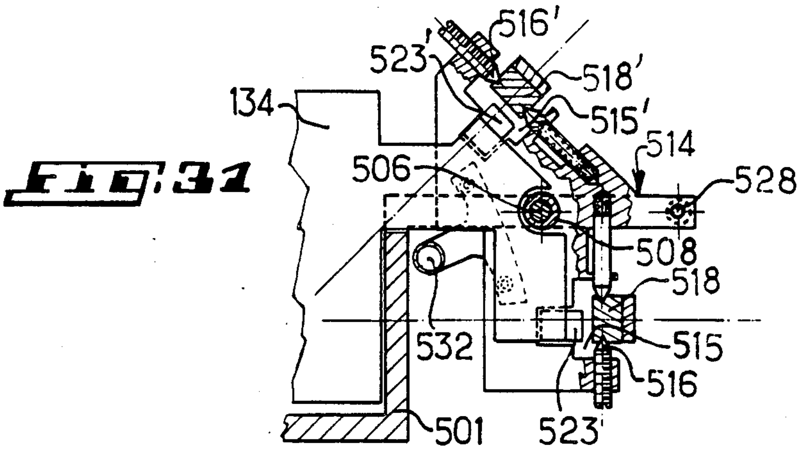
Figure 32:
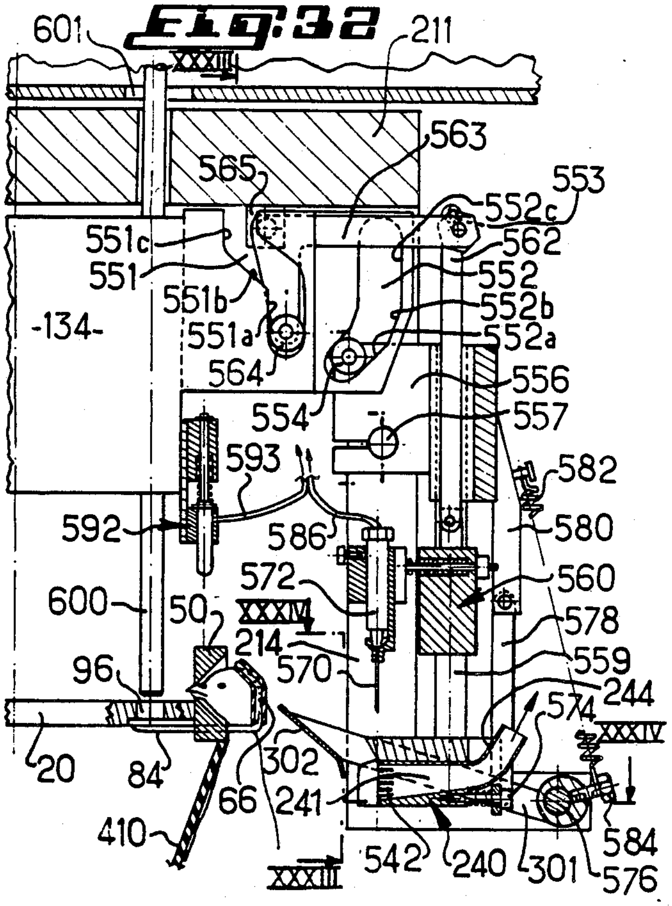
Figure 33:
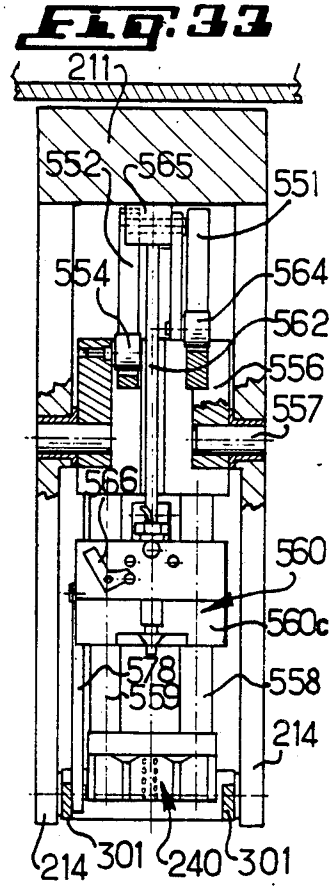
Figure 34:
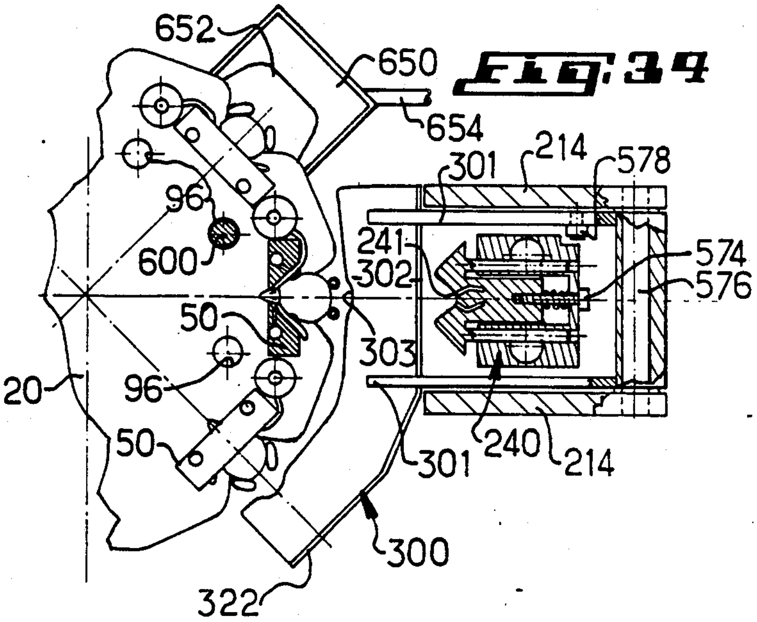
Figure 36:
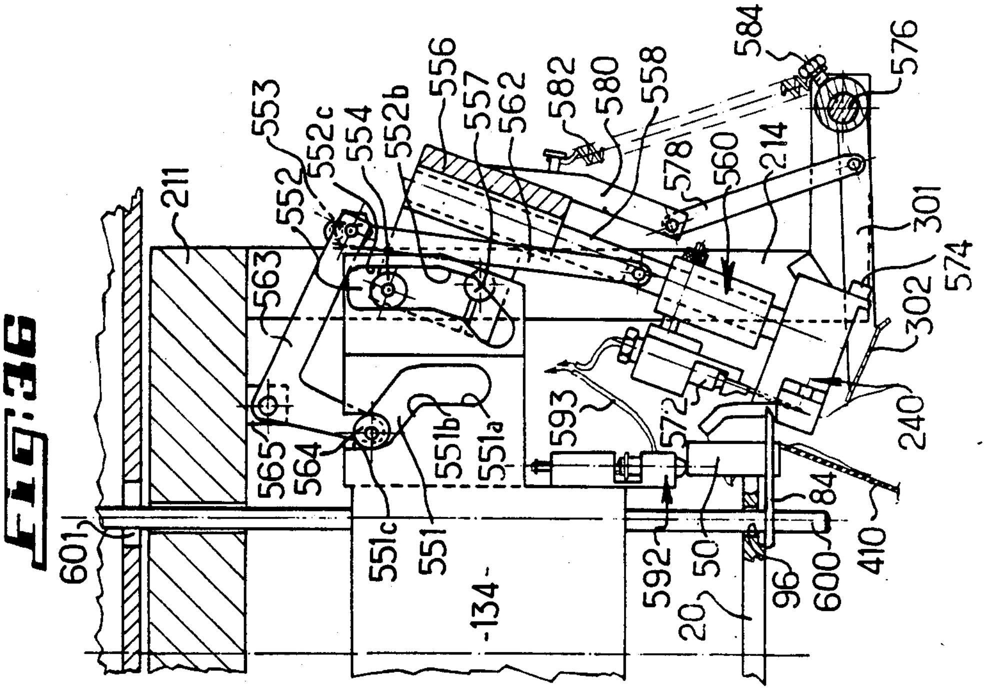
Figure 35:
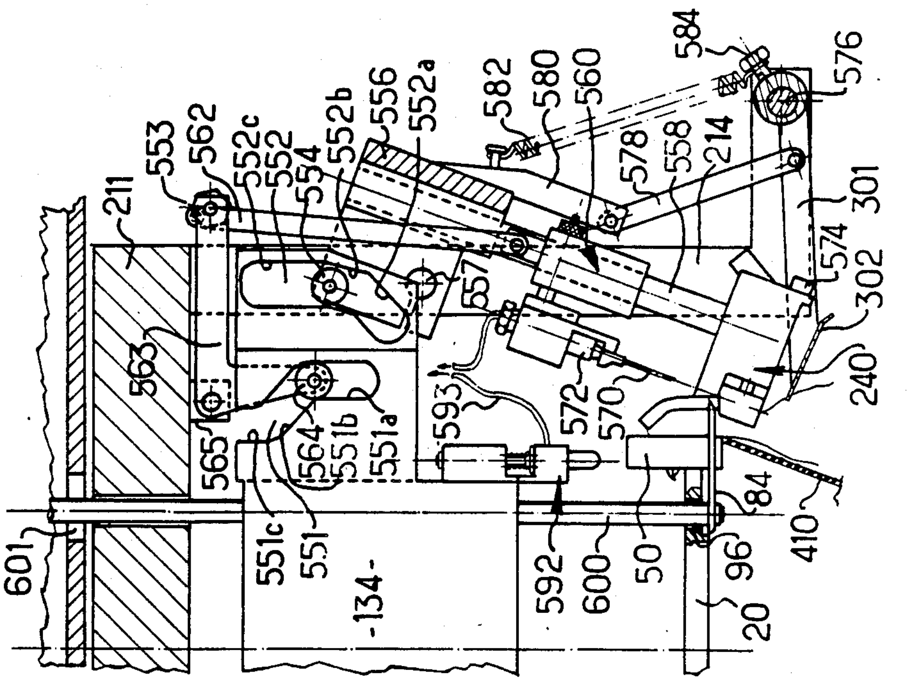

FIG. 6*a* presents a modification in the embodiment shown in FIG. 6 with some parts broken away;

FIG. 7 is a partial cross-sectional view of the endless circuit showing a held bird (as preferred treated animal);

FIG. 8 shows a front view of the debeaking assembly according to arrow VIII of FIG. 12;

FIG. 9 shows a detail of the debeaking assembly in operative position on the beak of the bird;

FIG. 10 shows a top view of the apparatus frame according to arrow X of FIG. 1;

FIG. 11 represents the actuator means according to line XI—XI of FIG. 10;

FIG. 11*a* is a detailed view of the actuating shaft, in lowered position, of mobile support which latter has only partially been lowered due to blocking either by a safety device comprising a rigid feeler, or by an external element impeding such a lowering movement of the mobile support;

FIG. 12 represents the top of the debeaking assembly with some parts broken away according to line XII—XII of FIG. 13;

FIG. 13 represents a view in longitudinal cross-section according to line XIII—XIII of FIG. 12:

FIG. 14 represents a view analogous to that of FIG. 12 with a partial cross-section, according to line XIV—XIV of FIG. 13, showing means allowing the modification of the movement of the debeaking element to modify the debeaking form;

FIG. 15 is a partial cross-sectional view according to line XV—XV of FIG. 10;

FIGS. 16 and 17 represent two embodiments of the debeaking element;

FIGS. 18, 18*a* and 18*b* are partial cross-sectional views at the station of administering a substance to an animal preferably a bird, showing more precisely a safety device preventing the administering of substance when no animal is supported by the facing support, the non-operative position being shown at FIG. 18 and the normal administering operative position being shown at FIG. 18*a;* FIG. 18*b* showing the case of action of the safety device;

FIG. 19 represents a side view of the assembly station of administering substance such as a liquid by spraying or atomizing, or another liquid by injection according to arrow XIX of FIG. 12, in non-operative position;

FIG. 20 represents a view analogous to that of FIG. 19 but in operative position;

FIG. 20*a* is an enlarged detailed view of a driving rod (220) shown at FIG. 20;

FIG. 21 is a cross-section according to line XXI—XXI of FIG. 19;

FIG. 22 is a partial view according to line XXII—XXII of FIG. 19, the suction device not being shown;

FIG. 23 shows a partial view in cross-section according to line XXIII—XXIII of FIG. 10;

FIG. 24 shows a partial view in cross-section according to line XXIV—XXIV of FIG. 10;

FIGS. 25 to 27 show an assembly for administering or applying a powder or an ointment notably with healing or calming action onto the beak(s) of a bird previously debeaked;

FIGS. 28 to 30 present another embodiment of the debeaking assembly; FIG. 28 showing the non-operative position for horizontal debeaking, FIG. 29 showing the operative position of said horizontal debeaking whereas FIG. 30 represents the nonoperative position of vertical debeaking;

FIG. 31 shows a partial view in cross-section according to line XXXI—XXXI of FIG. 29 showing a first debeaking assembly and a second cauterizing assembly;

FIGS. 32 to 36 show a most preferred embodiment of the substance administering assembly, FIG. 32 being a partial view in cross-section with parts partially broken away showing the non-operative position, FIG. 33 is a cross-section view according to line XXXIII—XXXIII of FIG. 32, FIG. 34 is a cross-section view according to line XXXIV—XXXIV of FIG. 32, FIG. 35 represents an intermediary position for which the syringe is not in operative position whereas FIG. 36 shows the operative position of the hypodermic syringe.

Figure 39:
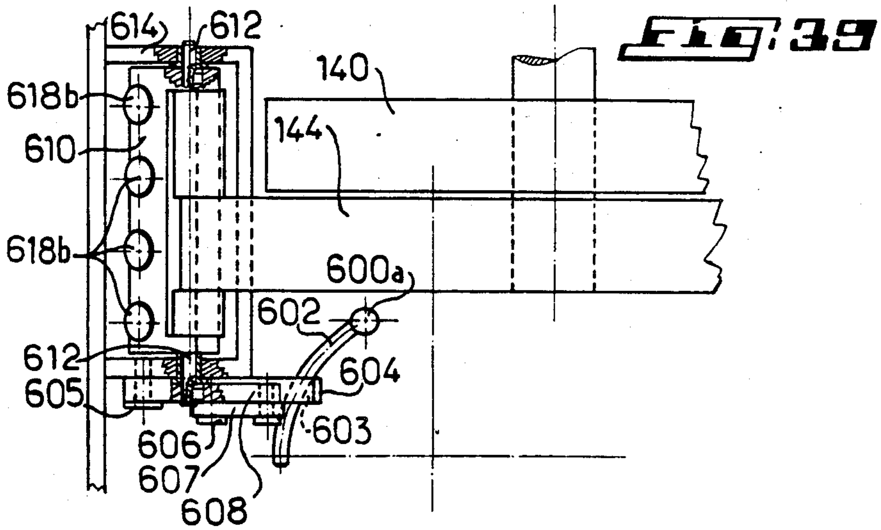
Figure 37:
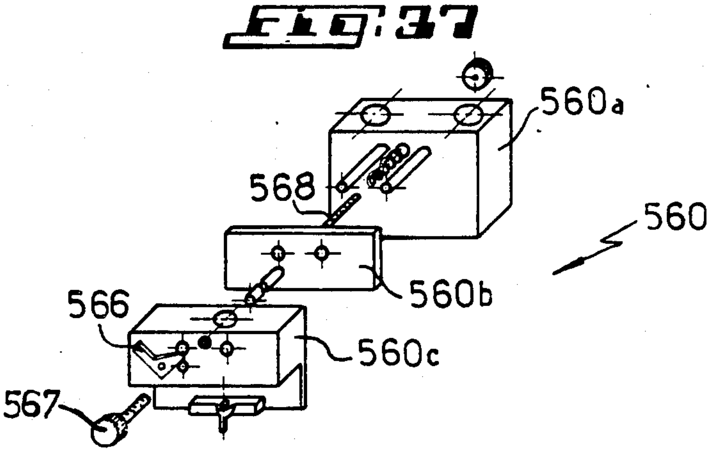
Figure 38:
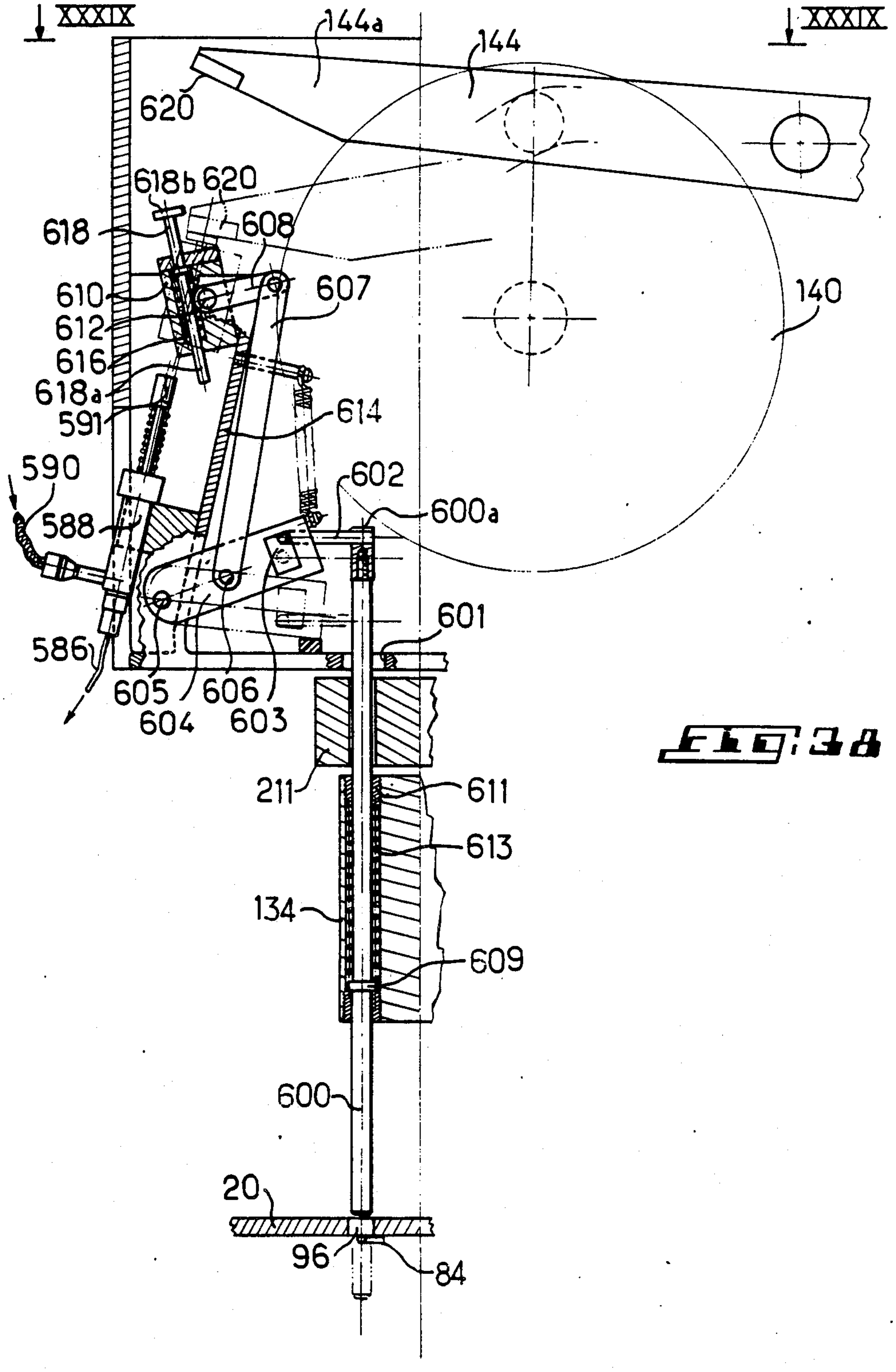

FIG. 37 shows a perspective view of the different parts constituting the syringe holder shown on FIGS. 32 to 36;

FIG. 38 shows the position of the substance dosage elements and another embodiment of the safety device, the actuating position being shown with faint lines; and FIG. 39 shows a top partial view of the safety device according to line XXXIX—XXXIX of FIG. 38.

Referring to FIG. 1, the invention apparatus, as in the case of prior U.S. Pat. No. 4,375,814 and its division U.S. Pat. No. 4,446,819 comprises a frame 1 mounted displaceable onto a support base 2 bearing on the ground. The apparatus comprises and endless circuit, for instance a table 20 relatively mounted onto the frame 1, supported by spindle 22 for rotation about axis 24 by motor 26 through a drive means 27 including variable speed drive transmission 28.

Turntable 20 has eight notches 21 at which are mounted animal holding means and/or supporting means called hereinafter animal supports 30 for receiving animals at loading station 31. Each animal support 30 preferably comprises means 32 for suspending an animal by its head with the head immobilized, with the remaining part of the body in space.

The apparatus further comprises at least one treating assembly (34,36,37) at the vicinity of the turntable 20, movable between an operative position and a non-operative position so that each support 30 is able to pass, upon rotation of the table 20 in the treating assembly station (35,38,39). For the treatment of animals, according to the present invention the treating assembly comprises an assdembly 36 for administering at least one treating substance, such as a liquid.

The apparatus of the invention also advantageously comprises an assembly 37 for administering or applying at least one powder, or ointment notably with healing or calming action, at administering station 39, essentially onto the beak(s) of a bird previously debeaked (see FIGS. 25 to 27).

Besides, in the case of treatment of birds as in previous U.S. Pat. No. 4,375,814 and its division U.S. Pat. No. 4,446,819, the apparatus can further comprise one or several additional treating assemblies which comprise one or several debeaking assemblies 34 at the debeaking station(s) 35. In the shown example; the debeaking station 35 is located before the substance administering station 38 but the order of said disposal is not important and can be reversed. Nevertheless ointment or powder administering station 39 is preferably located after the debeaking station 35 or after the cauterizing station when it is present as explained further.

Figure 4:
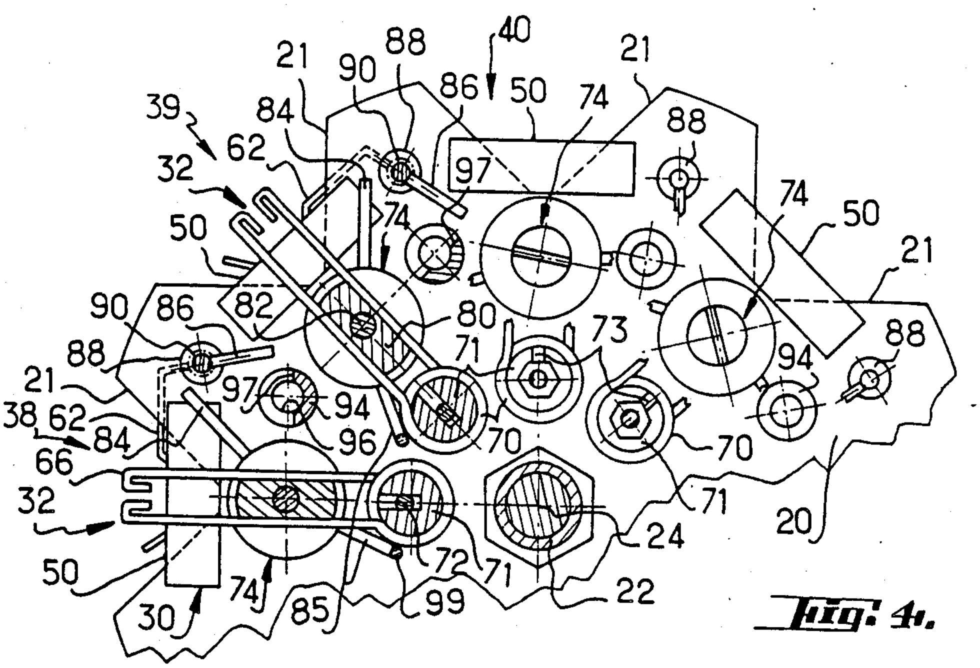
FIG. 4 is a partial underside view of the endless circuit.
Figure 5:
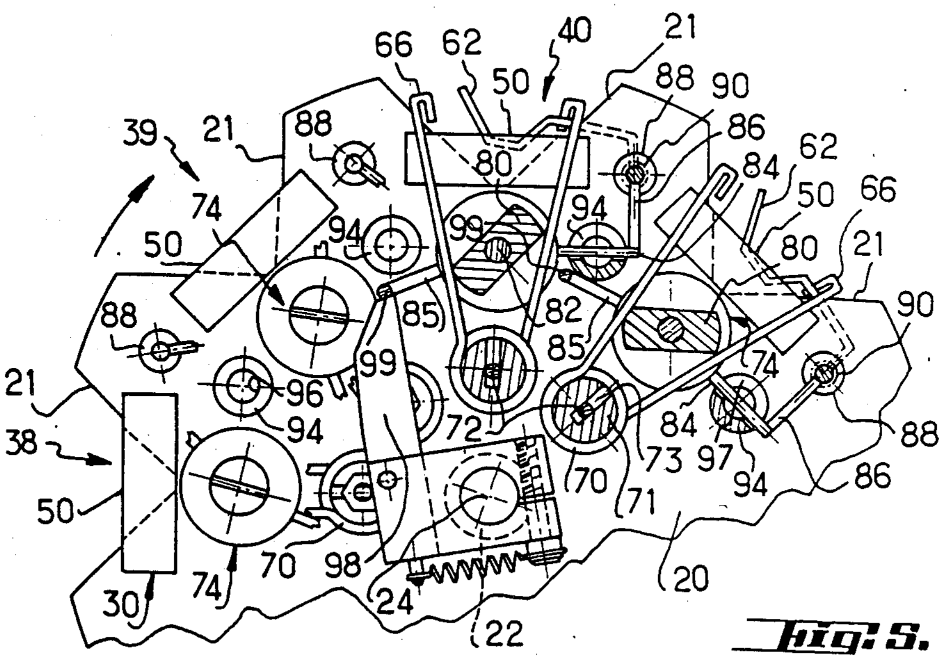
FIG. 5 is a partial underside view of the endless circuit near the unloading station.

The apparatus also comprises an unloading station 40 (see FIGS. 2, 4 and 5).

The invention apparatus further comprises actuator means 41 for actuating the treatment assemblies 34,36,37 to their operative position upon arrival of supports 30 to stations 35,38,39 and thereafter returning the treating assemblies 34,36 to their non-operative position (shown in FIG. 1). Suspending means 32 of each support 30 (FIG. 6) comprises a front piece 50 constituting at least a part of a headpiece, fixed at said table 20, and consisting of a metal block with a recess 54 for receiving at least a part of the animal's head. Rrecess 54 is preferbly conical and is shaped to snugly receive the head of the animal being treated. Front piece 50 is removable to allow substitution of various shapes.

In the case of treatment of a bird, front piece 50 also has an opening 56 at the apex of said recess 54 just large enough to admit the tip of the beak of the bird.

Each of said supports 30 further comprises a control member 62 constituted for instance by a rod located in the path of the animal being loaded into said support 30 and for this purpose it extends horizontally across recess 54, and is bent to extend into the recess. An alternative configuration for control member 62 is to extend straight across notch 21 below front piece 50, as at 62' in FIG. 6*a*, in which case it acts against the animal's neck rather than between its jaws or between its beaks in the case of a bird.

Suspending means 32 of each support 30 also comprises a pair of retainers 66 mounted on said table 20 for holding an animal's head in said recess 54. Retainers 66 are in the shown embodiment the free ends of, for instance, a coil spring 70 (FIGS. 3 to 5), and are shaped to extend across opposite sides of the animal's neck and then up along and against the back of the head. First portions 67 that cross the neck are curved to conform to the neck and to approach each other at 68 serving as a support for the lower maxiliary, where the retainers are bent up to form a vertical portion 69 curving at their free ends to conform to the animal's head.

Spring 70 is wrapped around disc 71, which is mounted on the underside of table 20 on post 72 which extends through slot 73 of the disc to allow radial adjustment (from axis 24) for varying the extension of retainders 66 according to the race and/or strain of the animal. From disc 71, retainers 66 pass between discs 76 and 78 of member 74, on opposite sides of bar-shaped eccentric cam 80 fixed between the discs. Discs 76 and 78 and cam 80 are mounted to pivot about axis 81 on shaft 82 which is fixed in table 20 for opening and closing retainers 66.

To control that opening and closing, arms 84 and 85 fixed to member 74 extend in generally opposite directions from shaft 82 and arm 86 extends from post 88 to act as a stop against arm 84 (FIG. 4), preventing clockwise (from the point of view of FIG. 4, looking at the underside of table 20) rotation of cam 80, which thus holds retainers 66 open against the force of spring 70. Post 88 is mounted in table 20 to pivot about axis 89 and has fixed to it above the table an end of rod 62. When arms 84 and 86 are against each other to hold the retainers open, rod 62 is pivoted somewhat outwardly from front piece 50. A spring 90 biases post 88 in this position.

Inward movement of control member 62 causes post 88 to pivot, moving arm'86 away from arm 84 to release the latter and allow spring 70 to close retainers 66, rotating cam 80 until it is aligned and balanced between the retainers (FIG. 4). To indicate whether retainers 66 are open or closed (and hence whether or not an animal is loaded between them), hollow post 94 is mounted in table 20 with its opening 96 positioned to be blocked by arm 84, which enters slot 97 of the post when the retainers are open. Post 94 thus also acts as a stop for arm 84, to protect the elastic limit of retainers 66, and acts additionally as a stop for arm 86 in its locking position (FIG. 7).

Finally, for driving the release of the animals, a release element, constituted for instance by a cam 98 is mounted on spindle 22 at unloading station 40 and is advantageously arranged in the path of downturned end 99 of arm 85 so as to pivot arm 85 and hence cam 80, counterclockwise (viewed, as before, from beneath the table 20) to the open position, whereupon spring 90 causes arm 86 in turn to pivot into place against arm 84, locking the mechanism open. It is thus clear that the above structure constitutes a linkage which, with the release element 98 together form release means for causing the support 30 to release its animal upon arrival at the unloading station 40.

In the case of treatment of birds, debeaking assembly 34 is then present (see FIG. 8) and comprises a debeaking element 110 with an open end shaped to fit over the end of the bird's beak. Although end 111 is shown in FIG. 9 with a circular cross-section, it may have other shapes, depending on whether one or both beaks are to be burned, and upon the degree and shape of debeaking desired. This shape can be the conical shape shown at FIG. 16 which is specifically adapted to perform simultaneously the debeaking of the two beaks or again the half-conical shape shown at FIG. 17 which is specifically adapted to perform the debeaking of the upper beak (in the shown position) or of the lower beak (in the reverse position). The debeaking assembly 34 also comprises means 112 to heat said debeaking element 110 to burn said beak. Said heating means 112 can be adjustable and can comprise a nozzle connected through tube 116 to a source of butane or other gas to provide a flame to debeaking element 110, typically to over 700° C. The debeaking assembly 34 further comprises means 113 for drawing off hot air around nozzle 114 to protect the apparatus from overheating and to remove debeaking products of combustion.

According to another embodiment the debeaking element 110 is electrically heated as shown, and explained further, with reference to FIGS. 28 to 30.

Advantageously, said means 113 for drawing off air comprises an exhaust tube 118, opposite nozzle 114, which is fed with a stream of fresh air by tube 115 connected to a larger tube 117. Ventilator means 119 blows air into tube 117. Debeaking element 110 extends between nozzle 114 and exhaust tube 118 and is fixed either rigidly or resiliently, in the vertical direction, to tube 117. It has to be noted that the free end of tube 118 is disposed at a location sufficiently spaced from said debeaking element 110, so as to avoid cooling the debeaking element 110 and above all end 111 which effects debeaking.

Drive means 27 driven by motor 26 and acting upon spindle 22 comprises as it can be seen from FIG. 10 a main shaft 120 having at one end a gear wheel 121 co-operating with an endless screw 122 on spindle 123 of pulley 124 with variable speed supporting a belt 125 actuated by pulley 126 also with variable speed fixed onto the arm 127 of motor 26.

The other end of main shaft 120 is connected through rigid coupling 128 to a secondary shaft 129 comprising an endless screw 130 co-operating with a cog-wheel 131 fixed onto spindle 22 of turntable 20. Of course the main and secondary shafts 120 129 are rotatively mounted with the aid of several bearing blocks 132, with respect to frame 1.

At least a part of the treating assemblies 34,36,37 is linked or mounted onto a mobile support 134, the latter being guided near one end **134*a* by spindle 22 to freely rotate and slide with respect to said spindle 22. The mobile support 134 is freely slidably mounted around an actuating shaft 136 of mobile support 134, mounted through a hole 137 provided therethrough at a location situated preferably opposite the end 134*a* of mobile support 134. It can be seen that mobile support 134 is freely slidably mounted around actuating shaft 136 with the aid of two bearing blocks, one of which 133 is located at the lower end of mobile support 134 constituting a stop means supporting a compression spring 138 located within hole 137, said spring 138 being further fixed to a ring 139 rigidly mounted onto actuating shaft 136. Said actuating shaft 136 is further connected to the actuator means 41** described herebelow.

Actuator means 41 comprises a wheel 140 rigidly mounted onto secondary shaft 129 constituting a double cam, each face comprising a cam path such as the cam path 141 shown in FIGS. 1, 10 and 11, the other cam path 142 being shown only on FIG. 10. Cam path 141 bears a roller 143 fixed to a lever 144 which is rotary articulated at one end onto an axle 145 rotatively mounted onto a bearing block 146, the other end supporting a vertical rod 147 mounted rotary articulated by a ball-and-socket joint 190 on said lever 144, the other end of vertical rod 147 being connected to actuating shaft 136 by another ball-and-socket joint 191 through a yoke 148 passing through a port 149 provided in frame 1. A driving rod 150 is fixed onto one end of axle 145 and at the other free end supports a pushing rod 151 with which it is articulated by a ball-and-socket joint 192. The other end of pushing rod 151 is rotatively articulated onto vertical rod 147 by a ball-and-socket joint 193. It can thus be seen that lever 144, driving rod 150, pushing rod 151 and vertical rod 147 form substantially an articulated parallelogram distortable in space. Preferably pushing rod 151 comprises two parts **151*a* and 151*b* threaded and connected with the aid of a sleeve 152 also threaded thereby varying the length of pushing rod 151 and rotation of mobile support 134. Also, yoke 148 and vertical rod 147 can be preferably threaded to vary the total length thereof and thereby provide adjustment of the vertical displacement of mobile support 134**.

In the other cam path 142 is located a roller 153 fixed to one end of a lever 154 fixed at the other end to axle 145 so as to rotate axle 145 and horizontally displace pushing rod 151 due to the vertical position of driving rod 150. Cam path 141 drives lever 144 which vertically actuates vertical rod 147 so as to raise or lower mobile support 134 during rotation of wheel 140. Cam path 142 horizontally rotates mobile support 134 and allows the latter to describe the desired arc with the aid of ball-and-socket joints 190 to 193.

In reference to FIG. 12, debeaking assembly 34 comprises three parts 160, 161, 162. Paart 160 comprises as shown in FIG. 13, two guiding members 163, 164 passing through holes 165, 166, respectively, through mobile support 134. Guiding member 163 is long enough to abut at its free end turntable 20, its free end being provided with a screw 167 for varying its total length. Part 161 comprises a finger 168 provided with a screw 169 interlinking part 162 to part 161. Part 162 comprises a spring hook 170 to hook a spring 171 between part 162 and hook 172 fixed on mobile support 134. Apertures 173, 174, 175 are provided respectively in parts 160, 161 and 162 to leave the passage to air tube 117 and gas tube 116. However, gas tube 116 and air tube 117 are fixed to part 162 by a clamping means 176.

As shown in FIG. 14, part 161 can be interlinked with part 160 with the aid of a screw 177 able to penetrate into a hole provided in part 160.

It can also be noted that part 161 comprises at its underside a further screw 178 (shown at FIG. 13) bearing on mobile support 134 when screw 167 does not already abut turntable 20. Besides, as it can be seen from FIGS. 12 and 13, finger 168 protrudes in recess 180 in part 160, the size of recess 180 being predetermined to allow parts 162 and 161 to pivot within determined limits when screw 177 does not engage part 160. In such a case, since air tube 117 pivots with part 162 and debeaking element is fixed to air tube 117, this will alow debeaking element to pivot to effect debeaking. In case screw 177 engages with part 160, parts 162 and 161 are fixed to part 160 and do not pivot. In this case debeaking element 110 only lowers vertically to effect debeaking of the upper beak.

In reference to FIG. 15 the mechanism to lower or raise frame 1 with respect to support base 2 is shown in more detail. This system comprises a crank 181 comprising an endless screw 182 so as to raise or lower frame 1 with respect to support base 2. Frame 1 advantageously comprises a blocking means 183 shown on FIG. 1 to block frame 1 in a determined position.

The assembly 36 for administering at least one substance to the animals comprises a part mounted onto turntable 20 and another part linked or mounted on mobile support 134 as can be seen more precisely in FIGS. 19 to 21. According to a feature of said substance administering assembly 36, it comprises means 200 for drop administering or spraying substance at at least one eye, at the nose, at the mouth or at other orifice of the animal, comprising advantageously at least a drop administering or spraying type syringe 200. The drop administering or spraying means comprises in addition at least one passage 58,60 realized in front piece 50 and extending from recess 54 to the external part of the front piece 50, said passage (58;60) provided with its filter (59;61) opening into recess 54 either at one eye position (passage 58, shown on FIGS. 19 and 20), or at a nose orifice position, or both (as shown on FIGS. 6, 6*a*), a drop administering or spraying type syringe being so mounted to provide substance to said animal through said passage (58 or 60) in operative position, as shown on FIGS. 2, 3 and 19 and 20.

Each drop administering or spraying type syringe advantageously comprises as syringe 200 a syringe body 201 and a syringe plunger 202 which latter can come into abutment on displacement of mobile support 134 against front piece 50. Body 201 is provided with a duct 203 opening in front of a filter 59 mounted above passage 58 so as to preferably tightly communicate therewith. On the other hand, the syringe body 201 also comprises a feeding duct 204 connected to a dosage element analogous to the dosage element 360, shown in FIG. 18 described further below. This dosage element is in turn connected to a reservoir of substance to be administered, for instance a medicine such as an antibiotic, a vaccine or other biological products, for instance vitamin products or products promoting growth or an aqueous solution or even water, each reservoir being disposed above each syringe to give a feeding through gravity.

It thus can be seen that said drop administering or spraying means comprises at least a substance distributing circuit (204-201-202-203,58-59) provided with a treating substance dosage element.

To administer a substance by the mouth of the animal, the drop administering or spraying means comprises advantageously a passage 63 realized within the control member 62 which is thus constituted by a hollow rod provided with substance administering orifice 64 at the level of recess 54 in regard of the animal's mouth and of substance feeding orifice 210 provided with a filter 65, and realized in post 88 continuously with passage 63 of rod 62.

The substance administering assembly 36 also advantageously comprises means for injecting liquid under the animal's skin, comprising at least a hypodermic syringe 206,207 and 208 linked or mounted onto mobile support 134 (FIGS. 19 to 21). The substance injecting administering assembly 36 comprises a plate 211 mounted at one end 211*a* and around spindle 22 in such a manner as to freely rotate with respect to said spindle 22 but without possibility of lowering or raising. This plate 211 is also provided with a hole 212 through which passes actuating shaft 136 for forcing in rotation said plate 211 since actuating shaft 136 is connected to the actuator means 41 previously described.

At end 211*b* of plate 211 is fixed a yoke 214 substantially located in vertical position and comprising at the free end thereof an oscillating support 216 mounted to freely oscillate with respect to yoke 214 with the aid of an intermediate axle 215 disposed substantially horizontally with respect to yoke 214.

To this oscillating support 216 are fixed two sliding rods 218 for syringe holder 219 holding syringes 206 to 208.

Syringe holder is driven in sliding movement with respect to sliding rods 218 by a telescopic driving rod 220 shown in detail in FIG. 20*a* passing through orifice 221 provided in oscillating support 216.

With reference to FIG. 20*a*, this driving rod 220 comprises a first piece 220*a* resiliently sliding within a second partly hollow piece 220*b* which retains it as well as a biasing spring 222. The end of driving rod 220 remote from syringe holder 219 is articulated in 223 on a cam support 224 fixed to mobile support 134. This cam support 224 comprises a cam 225 co-operating with the aid of the roller 226 rolling around an axle 227 substantially horizontally disposed on a roller supporting rod 228 the lower end of which is rigidly linked to the end of the oscillating support 216 opposite orifice 221 with respect to axle 215. Roller 226 is permanently biased against the cam profile 230 of cam 225 with the aid of the biasing spring 231 mounted onto a spring support 232 fixed on yoke 214.

The syringes 206 to 208 do not comprise plungers but communicate with the aid of feeding ducts 235,236 and 237 respectively, with a treating substance dosage element as 360 shown on FIG. 18, the operation of which will be explained further, each dosage element being of course connected to a proper substance reservoir, not shown, in the same manner as for syringe 200.

To the lower ends of sliding rods 218 is mounted a suction device 240 for drawing back the neck skin of an animal held in the said support 30 and it can be seen that each hypodermic syringe 206 to 208 is so mounted as to inject said treating substance under said drawn back neck skin, in the operative position shown in FIG. 20, subcutaneously.

Said suction device 240 comprises a perforated nozzle 241 provided with a perforated surface having one or a plurality of holes 242 extending vertically down a sufficient distance to provide drawing back a predetermined area of the animal's neck skin, in the operative position shown on FIG. 20. It can be seen (FIG. 21) that perforated surface 241 has a cross-section forming a V so as to be put onto and around the animal's neck. The upper surface 241*a* of perforated nozzle 241 comes by end of stroke into abutment against retainers 66.

The suction device 240 is connected to a vacuum pump not shown with the aid of a suction pipe 244 which goes up within the frame 1 as it can be seen on FIG. 10 in which it is fixed with the aid of a holding piece 245 where suction pipe 244 is divided into two secondary suction pipes 246 and 247.

Secondary pipe 246 is connected to the vacuum pump not shown whereas the other secondary suction pipe 247 comprises an opening 248 which can be put in communication with the atmosphere with the aid of suction breaking element 250 during a period of time where said suction is unnecessary between two successive injection administering operations.

This suction breaking element 250 is better shown on FIG. 24 and comprises a cam disc 251 fixed onto main shaft 120 and it can be seen on FIG. 24 that this cam disc 251 is not fully circular but a part thereof has been cut so as to provide a free angle α predetermined to provide a rotating time of the main shaft 120 commensurate with said period of time where said suction is unnecessary between two successive injection administering operations. Indeed, when the cam disc 251 is active and fluid-tightly applied against opening 248 of secondary pipe 227, a suction is performed through suction pipe 244.

The invention holding and/or supporting means also comprises means 300 for holding the back of said animal rearwardly immobilized with respect to the turntable 20 at each treating assembly station to maintain the animal's body preferably substantially vertical in operative position as shown on FIG. 20.

Said animal's back holding means 300 is actuated by actuator means 41 through a connection by levers and rods articulated with them and by a wheel 310 mounted on the driving shaft 120 which will be explained in detail herebelow.

Thus, the animal's back holding means 300 comprises a generally U-shaped positioning element 301 onto which is fixed, at the free ends of the U, an elastomeric membrane 302 provided with a recess 303 for positioning the animal's back.

Positioning element 301 is supported by two actuating shafts 304 and 305 going up into the frame 1 by passing through a hole 306 of frame 1 and being fixed to a cross-piece 307 appearing on FIGS. 10 and 23.

Said cross-piece 307 is itself supported while being rotary articulated by a knee joint with a vertical rod 308. The upper end of vertical rod 308 comprises a horizontal extension constituting a horizontal rod 309 which is rotary articulated by another knee-joint onto the free end of a driving lever 310 articulated at the other end 310a on a bearing block 311 fixed to frame 1.

Driving lever 310 comprises a roller 314 at the location remote from the articulating axis 312 of end 310a of driving lever 310 with respect to bearing block 311. This roller 314 is disposed within a cam path 316 of a cam wheel 320 fixed to main shaft 120. This cam path 316 is foreseen to provide a raising or lowering and rotating motion analogous to those provided by cam paths 141 and 142 of wheel 140 previously described for mobile support 134.

As shown on FIG. 22 the positioning element 301 can materially support a pre-positioning arm 322 in the case where the animals to be treated are birds to be debeaked, said pre-positioning arm 322 thus extending laterally up to the debeaking station previously described so as to pre-position said birds during debeaking. Said pre-positioning arm 322 also extends vertically downwardly and with a tilted surface 326 with respect to the vertical so as to avoid rearwards movements of said birds during passage of said birds from debeaking station to substance administering station. At the free end 323 of pre-positioning arm 322 are mounted elastomeric membranes 324 provided with a recess 325 to snugly hold the animal's back.

In addition, elastomeric membrane 302 can comprise a slot 330 for allowing free passage and pivot of sliding rods 218 supporting syringe holder 219 through the space 331 appearing within the U-shaped positioning element 301.

The apparatus of the invention advantageously also comprises a safety device 340 shown more precisely on FIG. 18 for preventing administration of substance when no animal is supported on a support facing the administering assembly.

This safety device 340 in the shown embodiment comprises a feeling means 341 linked in displacement to the mobile support 134 and thus to the substance administering assembly, and a stop means with respect to the feeling means interposing the path of the feeling means when no animal is supported on the support facing the substance administering assembly, said stop means being constituted by arm 84 interposing in hole 96 as shown on FIG. 5.

Said feeling means 341 can be constituted either by a vertical stop means screwed onto mobile support 134, or preferably by a vertical rod screwed onto mobile support 134 as shown on FIG. 18 and comprising a cam element 355 slidably mounted on rod 342, having an elongated part 355a at its free end and provided with a through hole 356 ending within said elongated part 355a with a larger inner cross section 356 a allowing sliding of shoulder head 357 of vertical rod 342. Said cam element 355 is permanently biased against shoulder 357 by a spring 358. Said cam element 355 has a double tilted profile 343,344 abuting an apex 345.

Against these tilted cam profiles 343 and 344 is permanently biased a roller 346 of a cam follower 347 substantially horizontally disposed within a hole 359 of a bearing block 348 mounted around spindle 22 and fixed onto a vertical support 349. Cam follower 347 horizontally linearly slides with respect to said vertical support 349 which is itself fixed onto previously described plate 211 to rotate with it.

Cam follower 347 bears at its free end 347a a displaceable stop means 350, bearing on flange 348a of block 348. Said displaceable stop means 350 with cam follower 347 is permanently biased against cam element 355 of feeling means 341 with the aid of a biasing spring 500.

The displaceable stop means 350 has an upper surface 352 substantially horizontally disposed and is provided with a traversing orifice 353 substantially vertically disposed.

The respective dosage elements of the drop, spraying or injection substance administering assemblies are fixed to the mobile support 134. One dosage element 360 is shown on FIG. 18 and comprises a body 361 the lower end of which is provided with a plunger 362 which is disposed substantially above displaceable stop means 350 so that when mobile support 134 lowers, said plunger 362 either comes into contact with upper surface 352 of displaceable stop means 350 if the feeling means 341 can freely lower through orifice 96 of turntable 20 when an animal is present (as shown on FIG. 18a) so that plunger 362 is actuated inwardly with respect to body 361 to feed a predetermined liquid dose by substance feeding duct 235 for instance; or if no animal is present plunger 362 lowers freely within orifice 353 due to the rearward movement of cam follower 347 driven by tilted cam profile 343, as shown on FIG. 18b.

It can be noted that at unloading station 40, the animals can be counted with the aid of any counting device known per se and which has thus not been represented.

Another way of counting the animals is to provide a counting device 400 onto mobile support 134 comprising a flexible foil 401 which can be biased by contacting the animal's head against an appropriate sensor 402 for instance electromagnetic, as shown in FIG. 20, and emits a signal which acts on a counter to add one unit.

Finally, the turntable 20 is surrounded by an elastomeric membrane 410 tilted as shown in FIGS. 19 and 20 so as to form a soft forward stop means of the animal's front part, notably the members thereof and constituting means for holding the front of the animal forwardly immobilized It can finally be noted that actuator means 41 are such that treating assemblies 34,36,37 are moved through their complete cycles the same number of times as the number of supports 30 provided on table 20 for each complete rotation of table 20.

Now, the operation of the above described invention apparatus will be described.

In operation, an operator loads an animal which can be preferably a bird, into each support 30 as it reaches station 31 by squeezing the back of said animal against control member 62 or 62′ to close retainers 66, as described above, and forces (with the help of the conical surface of recess 54) the mouth to close and go through front piece hole 56.

In the case of treatment of birds, a debeaking station 35 is preferably present. As table 20 rotates and a loaded bird approaches debeaking station 35, mobile support 134 is caused by actuator means 41 previously described to descend towards table 20 and causing thereby debeaking assembly 34 to also descend and pivot outwardly towards support 30 whether an animal is present or not at debeaking station 35. When guiding member 163 abuts against table 20, the downward motion of part 160 of the debeaking assembly ceases. However, as described in previous French patent application No. 79 23 018, when screw 177 does not engage part 160, continued downward motion of mobile support 134 causes parts 162 and 161 to pivot downwardly under the influence of spring 171, causing air tube 117 and gas tube 116 to pivot thereby also pivoting horizontally debeaking element 110 through a predetermined rotation until it receives and presses against the tip of the bird's beak protruding through hole 56. Throughout the operation, the positive air flow from tube 115 into exhaust tube 118 induces air flow near front piece 50, into tube 118, removing excess hot air to avoid overheating the bird or the parts it touches, cooling front piece 50, and also removing products of combustion when the beak is burned.

If it is desired to effect only the debeaking of the upper beak of the bird, as described in inventor's prior French patent application No. 79 23 018, screw 177 is engaged into part 160 to interlink parts 162 and 161 with part 160. Thus, a downward motion of part 160 caused by downward motion of mobile support 134 will only provide vertical downward motion of debeaking element 110 onto the upper beak to be debeaked by burning.

Upon completion of the debeaking, after a predetermined period of time provided by the cam paths of wheel 140 of actuator means 41, mobile support 134 begins to rise, and begins to rotate parts 161 and 162 by acting upon screw 178 and when screw 177 is not engaged with part 160 debeaking element 110 is withdrawn horizontally from the bird, and further upward motion of mobile support 134 also causes an upward motion of debeaking assembly, the latter moving quickly upwardly to its starting position.

Also whether an animal is present or not at debeaking station 35, another animal can or cannot be at substance administering station 38. Because at least a part of treating assembly 36 is linked to mobile support 134, the said motion of mobile support 134 displaces said linked part of administering assembly 36 from its non-operative position shown in FIG. 19 to its operative position shown in FIG. 20 due to the lowering of cam support 224 and driving rod 220 with respect to oscillating support 216 and sliding rods 218 with correlated forward pivot of oscillating support 216 caused by roller supporting rod 228 biased against cam 225.

In addition, due to the profile of cam path 316, the animal's back holding means 300 also descends and the elastomeric membrane 302 lowers behind the neck of the animal and progressively tilts to the back thereof to hold said animal substantially immobilized in vertical position. Since said animal 280 is also biased against elastomeric membrane 410 said animal 280 cannot practically move or make disordered movements.

It must be noted that, preferably, holding means 300 comprise a pre-positioning arm 322 so that an animal 280 is pre-positioned by elastomeric membrane 324 at the previous station which can be a debeaking station in the case of debeaking birds.

Since suction device 240 is fixed to the lower ends of sliding rods 218, the suction device also comes into the operative position shown in FIG. 20 in abutment against retainers 66 while suction is performed since opening 248 of secondary suction pipe 247 is closed by the surface of cam disc 251. This suction results in the drawing back of the neck skin not maintained between retainers 66, against the perforated surface 241. Due to the V conformation of perforated surface 241, continued suction stretches the skin sufficiently to permit insertion of at least one needle 260, 261, 262 of at least one hypodermic syringe 206, 207, 208 respectively supported by syringe holder 219.

During this descent of mobile support 134, needle 260, 261, 262 enters the animal's stretched neck skin (FIG. 20), due to the fact that feeling means 341 enters opening 96 of post 94 since with an animal supported between retainers 66 at station 38, opening 96 is not closed and allows the passage of feeling means 341 and in this case as shown on FIG. 18*a*, cam follower 347 has passed over apex 345 of feeling means 341 so that displaceable stop means has been displaced in the direction of feeling means 341 so that the upper surface 352 of stop means 350 is located in the displacement of each dosage pump means 360 so that plunger 362 will abut said upper surface 362 and will be actuated within body 361 and will feed a dose of a treating (preferably liquid) substance in the corresponding syringe either of drop or spray 200 or injection 206,207 or 208 and hence, either by drop or spray; or subcutaneously in the animal's stretched skin. As shown in FIG. 21, the length of needles 260,261 and 262 is different to inject liquid drops at different depths. The depth of penetration of needle 260,261 or 262 is adjustable by changing either the needle or the position of the syringe 206,207,208 or the length of driving rod 220. Telescopic driving rod 220 allows the needle penetration to stop at the predetermined depth during or even before injection.

Simultaneously, also the contents of the syringe body 201 of the drop administering or spraying means 200 fed by said dosage elements such as 360, are discharged because as support 134 continues down, plunger 202 of each drop administering or spraying means abuts its associated filter 59,61 or 65 and said plunger 202 enters syringe body 201 and injects the liquid contained therein for instance by passage 58 to a nose orifice via duct 203.

By the end of drop administering or spraying and injecting operations, suction is released since opening 248 of secondary suction pipe 247 is now open to atmosphere due to the cut portion 253 of angle $\alpha$ of cam disc 251, causing thereby notably an automatic cleaning of suction pipe 244.

During the return motion towards the starting non-operative position of mobile support 134, springs such as 363 (FIG. 18) provided around the plunger of each dosage pump means either of the drop administering, or spraying means, or the injection means, force the corresponding plungers outwardly, drawing substance from the reservoirs back into said bodies. This cycle to cycle exchange of substance between the reservoirs and the bodies of the dosage pump means 360, 200 for instance can optionally promote a desirable mixing between each reservoir if this is wished.

For maximum dosage accuracy, passages 58, 60, 210 and 63 and the filters 59, 61 and 65 should be filled with the treating substance (and will retain it by capillary action) before start up the apparatus.

In the case of a rigid feeler, if retainers 66 are open, passage of feeler would is blocked by arm 84 causing thereby the stoppage of downward movement of mobile support 134 (FIG. 11*a*) and the dosage elements mounted onto mobile support 134 are thus not actuated since plungers 362 cannot come into abutment against turntable 20.

In the preferred case of a telescopic feeler as shown on FIGS. 18, 18*a*, 18*b*, should retainers 66 have been open, end 355*a* of feeling means 341 would have been blocked by arm 84 so that during further downward movement of mobile support 134 the cam follower 347 will remain against cam apex 345 (FIG. 18*b*) due to sliding of vertical rod 342 within larger hole part 356*a* and the orifice 353 of displaceable stop means 350 is located in the path of plunger 362 so that said plunger 362 can lower freely and is not actuated thus preventing administration of substance.

The invention apparatus can further comprise preferably a treating assembly 37 for administering or applying a powder, or an ointment, notably with healing or calming action, essentially onto the beak(s) in the case of treatment of previously debeaked birds.

This treatment which can take place at station 39 improves the healing as well as the calming of the pains due to the debeaking.

Said station 39 for applying a powder or ointment must, of course, be practically compulsorily located after the debeaking station 35 or after cauterizing station. In the shown example, the powder or ointment applying station has been located after the vaccinating station 38 but it can naturally be located before.

The treating assembly 37 comprises according to the embodiment shown in FIGS. 25 to 27, a yoke 420 substantially vertically located and fixed to rotative plate 211. The lower part of said yoke 420 is divided into two arms 422 and 424 the free end of which supports an axle 426 rotatively mounted with respect to arms 422, 424.

Onto this axle 427 is rigidly mounted a pivoting rod 428, at a location spaced from its upper 428*a* and lower 428*b* ends so as to allow a displacement of said ends through rotation of the said rod 428-axle 426 with respect to arms 422–424.

At the upper end 428*a* of pivoting rod 428, is fixed one end of a resilient return means 430 constituted by a spring, the other end of which is fixed onto yoke 420.

In addition, mobile support 134 is provided in front of said pivoting rod 428 with a cam 432, the profile of which is located substantially vertically and comprises at its lower part a shoulder 434.

An adjustable cam follower means 436, for instance constituted by a finger, is appropriately fixed onto pivoting rod 428, namely generally between the upper part 428*a* of pivoting rod 428 and pivot-axle 426.

Pivoting rod 428 comprises further, preferably at its lower part 428*b*, clamping means 438, 440 such as clips, supporting, for instance through ratchet mechanism, a means 442 for administering or applying a powder, or ointment, for instance constituted by a tube provided at its lower part with a piece of distributing or applying means 444 constituted for instance by a felt piece in the case of administering a relatively fluid ointment. The free end of felt 444 is conformed to the bird's beak with the view to be able to apply for instance said ointment on the whole surface of the beak(s) of bird 280.

It must be noted that the respective positions of cam 432 with its shoulder 434 and cam follower means 436 are such that the cam follower means takes support against shoulder 434 in the non-operative position shown on FIG. 25, having caused thereby the pivot in the direction of mobile support 134 of lower part 428*b* of pivoting rod 428 and thus the withdrawing of ointment or powder administering means 442 from the bird's beak 280 (FIG. 25).

Besides, during the descent movement of mobile support 134, cam follower means 436 has been brought nearer to mobile support 134 by passing onto the upper profile 433 of cam 432 so that pivoting rod 428 is now located substantially in the vertical position shown in FIG. 26. In such a position, the powder or ointment administering means is in operative position, as can be well seen in FIG. 26.

It must be noted that said powder or ointment applying or administering assembly can very well serve in its essential constituents to realize the debeaking assembly 35 since it is then sufficient to replace administering means 442 for the debeaking element to obtain a debeaking assembly.

This can be preferably performed so as to obtain two treatment assemblies having the same essential constituents, thereby minimizing the total piece number to manufacture to realize the invention apparatus.

At unloading station 40 birds are automatically released and can be counted, as already described. At vaccinating station 36, the animals can be counted with the aid of flexible foil 401 biased by the animal's head as shown on FIG. 20 against the abovesaid sensor 402 which adds one unit to a counter.

Displacement of stop means 350 can also be detected and be used to add one unit to a counter.

Overall, operation is simple and foolproof, and permits highly controlled treatment at extremely high speed, for instance, as fast as 6000 animals, and preferably birds, such as chicks, young guinea-fowls, young turkeys, per hour.

It must be noted that when the safety device comprises a rigid feeler, spring 138 is not compulsory within mobile support 134 around actuating shaft 136 unlike as shown in FIGS. 11, 11*a*.

In the case of safety device 340 comprising a telescopic feeler 341, no spring 138 is necessary to be placed within mobile support 134 around actuating shaft 136 but its presence constitutes a safety against an external mechanical blocking or locking of mobile support 134.

In reference to FIGS. 28 to 30, another embodiment of debeaking assembly 34 is shown.

This debeaking assembly 34 is in fact an improvement of the basic structure of the ointment applying assembly shown in FIGS. 25 to 27.

Thus, in this improvement, the plate 211 comprises a downwardly oriented vertical part 501 provided with a horizontal arm 502 whereas the plate 211 also comprises an upper horizontal arm 504, the free end of said arms 502 and 504 being connected through a vertical rod 506 surrounded by a sleeve 508 having its upper part threaded and two nuts 509 and 510 screwed on said threaded part. On the other hand, a nut 511 is positioned between arm 504 and the nuts 509,510, a spring 512 being located between nut 511 and sleeve 508. The lower part of sleeve 508 bears an element 514 in substantially horizontal location and comprises an opening 515 wherein is located a horizontal axle 516 constituting the rotation axis located at the lower end of a vertical cam follower 518 at the upper end of which is articulated a roller holding element 519 provided with a roller 520 following a cam profile 521 defined on the exterior part of a substantially vertical cam element 522 linked through a horizontal portion 522*a* to mobile support 134. It must be noted that the lower end of the cam 522 comprises an outwardly disposed shoulder 523 on whch bears the roller in the non-operative position for horizontal debeaking as shown in FIG. 28. The cam follower 518 is biased against cam profile 521 due to the biasing action of a spring 525 having one end fixed onto cam follower 518 and the other end on horizontal element 514. Horizontal element 514 bears on a screw 527 screwed at the free end of arm 502 with its head downwardly located and its threaded end co-operating with a slot 528 provided in the lower external part of horizontal element 514, thereby allowing the working height of the debeaking element(s) 529 and/or of the cauterizing element 529' to be set.

On the other hand, a debeaking element 529 is fixed to cam follower 518 so as to be settable at a proper level or height and so as to rotate with it. Also, the debeaking or cauterizing element can be laterally set through action on the rotating axle of cam follower 518 (FIG. 31). Debeaking element 529 is electrically heated as understandable from the drawing of electric wires 530.

The free end 529*a* of debeaking element 529 is conformed to the beak of the bird 280 like end 111, and can be replaced for another element as shown in FIG. 30 to perform a vertical debeaking.

The burnt products are sucked through duct 532.

It must also be noted that cam follower 518 bears an adjusting screw 534 allowing the angular displacement of cam follower 518 and thus of debeaking element 529 to be set.

Thus, from the non-operative position shown in FIG. 28, the lowering motion of mobile support 134 causes the cam follower 518 to rotate inwardly and debeaking element 529 comes into abutment against the beak of the bird 280 as shown in FIG. 29. The displacement of free end 529*a* is substantially horizontal and thus this debeaking is called horizontal debeaking and allows debeaking by burning the upper and lower beak(s).

When only the upper beak must be debeaked (through burning) a vertical debeaking enabled by the invention apparatus merely by screwing nuts 509 and 510 on the threaded part of sleeve 508 as can be seen clearly by comparison of FIGS. 30 and 28.

FIG. 31 shows the provision of a debeaking assembly and a cauterizing assembly, both said assemblies being here realized with the same essential structural elements so that the cauterizing assembly elements analogous to those of the debeaking assembly elements are given the same reference number plus the sign '. Accordingly, everything that has been said for the structure and the function of the debeaking assembly is applicable to the cauterizing assembly.

Nevertheless, to yield cauterization one can modify the form of the end 529*a'* of the cauterizing element 529' to adapt it to the particular previously effected debeaking and this also applies to the heating temperature of the cauterizing element 529'.

This structure of the debeaking assembly is usable for providing an ointment applying assembly as previously described.

In FIGS. 32 to 39 the most preferred embodiment of substance administering assembly is shown. More particularly in FIGS. 32, 33 and 35, 36 one can see that the substance administering assembly is as follows:

Mobile support 134 comprises a first cam formed by a slot 551 having the specific profile shown on FIG. 32, namely first vertical portion 551*a*, an inwardly tilted portion 551*b* and a last vertical portion 551*c*. Said mobile support 134 also comprises a second cam 552 also formed by a slot comprising an outwardly tilted lower portion 552*a*, an intermediate differently tilted portion 552*b* and a last substantially vertical portion 552*c*.

The second slot 552 bears a roller 554, the axle of which is fixed on an oscillating support 556, itself articulated on an axle 557 fixed onto the vertical yoke 214 of plate 211. The oscillating support 556 is thus analogous to the oscillating element 216 of the embodiment shown in FIGS. 19 and 20. This oscillating support 556 accordingly bears two sliding rods 558 and 559 better shown in FIG. 33. A syringe holder 560, analogous to syringe holder 219 of FIGS. 19 and 20, is slidably mounted onto sliding rods 558 and 559 and is driven by a driving rod 562 articulated by an eccentric element 553 on an L-shaped lever 563 bearing at the other free end a roller 564 located in the first slot 551. The eccentric articulation 553 allows the depth of penetration of the needle in the vertical direction to be set. The L-shaped lever 563 is also articulated at the base of the L to a protrusion 565 of plate 211.

The structure of syringe holder 560 is better shown in FIG. 37 and comprises in fact three parts, a bottom part 560*a* sliding on sliding rods 558 and 559, an intermediate part 560*b* and an outer part 560*c* bearing at least one hypodermic syringe. The hypodermic syringe is locked on outer part 560*c* through a locking means 566. The external part 560*c* is fixed to intermediate part 560*b* by an attachment means 567. An adjustment screw 568 is provided so as to precisely set the position in distance of elements 560*b* and 560*c* with respect to bottom element 560*a*, thereby precisely adjusting the depth of penetration, in the horizontal direction, of needle 570 of hypodermic syringe 572 to which it will penetrate under the neck skin of the animal 280.

Furthermore, the lower ends of sliding rods 558 and 559 bear the suction device 240 shown in FIGS. 19 and 20 with a perforated nozzle 241 provided with a perforated surface connected to suction pipe 244 as shown in FIGS. 19 and 20. It can here be noted that an adjustment screw 574 sets the position of the perforated nozzle 241 with respect to retainers 66 so that both needle and nozzle are independently settable not only one with respect to the other but with respect to the held animal.

Also, as in FIGS. 19 and 20, the holding and/or supporting means comprises means 300 for holding the back of said animal rearwardly immobilized with respect to the endless circuit constituted by turntable 20.

This back holding means comprises as in the embodiment shown in FIGS. 19 and 20, a generally U-shaped positioning element 301 onto which is fixed, at the free ends of the U, a piece 302, resilient or flexible or pliable, provided with a recess 303 for positioning the animal's back, and a prepositioning arm 322.

Positioning element 301 is rotatively mounted at the base of the U, onto the external part of yoke 214 of plate 211 with the aid of an axle 576.

Furthermore, at a location spaced apart from the base of the U said positioning element 301 is articulated onto a holding-rod 578 having its upper end also articulated onto an arm 580 fixed onto oscillating support 556. Arm 580 bears one end of a spring 582, the other end of which is fixed onto a screw 584 screwed on positioning element 301 so as to permanently draw the positioning element into the operative position. FIG. 32 shows the non-working or non-operative position of the assembly since mobile support 134 is in non-operative position.

It can be observed that the articulation points of rod 578 are such as to avoid any interference between the movements of the suction device and positioning element 301.

It can further be observed with hypodermic syringe 572 has no plunger but communicates with the aid of feeding pipe 586 to a treating substance dosage element 588, itself connected through an input pipe 590 to a proper substance reservoir not shown. Of course, each hypodermic syringe has a separate substance dosage element so as to feed generally a different substance, and accordingly, for instance, different vaccines can be administered through injection.

In this embodiment, the mobile support 134 bears the drops or spraying syringes 592 basically analogous to spraying syringe 200 shown in FIGS. 19 and 20. Spraying syringe 592 of course communicates through a feeding pipe 592 to a substance dosage element similar to the substance dosage element 588 shown in FIG. 38, itself connected to a proper reservoir not shown.

Thus, in this embodiment, the substance dosage elements are fixedly mounted onto the apparatus frame.

Now the safety device of this most preferred embodiment will be described.

The safety device here comprises a feeling means 600 constituted by a vertical rod analogous in principle and in function with those previously shown in connection with the other embodiments. Feeling means 600 comprises a collar 609 and a spring 613 which is located around rod 600 while being compressed between a bearing 611 and collar 609. This vertical rod passes through mobile support 134 while being guided thereby and also through rotating plate 211 and through a slot 601 provided in the bottom of the apparatus frame. The upper part 600*a* of feeling means bears a substantially horizontal arcuate arm 602 located in one opening 603 provided within a lever 604 articulated on the apparatus frame through an axle 605 (FIG. 38).

At a location 606 spaced apart from axle 605 is articulated a driving rod 607 itself articulated onto a push-rod 608.

Push-rod 608 is itself articulated onto an oscillating element 610 rotating with the aid of an axle 612 on a U-shaped element 614 fixed onto the frame (FIG. 39).

Oscillating element 610 comprises several cavities like the cavity 616, shown in FIG. 38, in which are located pushers 618 having a free lower end 618*a* and a top head end 618*b*. When an animal is held, and the feeling means 600 can freely lower through orifice 96 of turntable 20, the oscillating element 610 is so positioned as to be able to either actuate the plunger 591 of the dosage elements 588 or to be actuated by a protruding part of lever 144 moved in displacement by wheel 140 and having a lowering and raising motion. Free end 144*a* of lever 144 has fixed thereto a cushion 620 which during downward motion of lever 144 pushes the plungers 618 of the oscillating element 610. The actuating position is shown with faint lines. Cushion 620 comprises a resilient part for compensation of stroke defects or manufacture defects.

It is clear that when no animal is held arm 84 obturates hole 96 so that the feeling means 600 cannot freely descend and arcuate arm 602 will not pivot lever 604 and the oscillating element 610 will not be moved so that the lowering motion of lever 144 will not be able to cause an inward motion of plungers 591 of substance dosage elements 588.

By considering FIG. 32 showing the non-operative position, FIG. 35 showing the intermediate position wherein only the back holding means and the suction device are in operative position but not the syringe holder, and FIG. 36 showing the operative position both for injecting substance and applying spray or drops of substance, the operation of the substance administering assembly is clearly understandable. Such movements are caused by the specific profile of slots 551 and 552. This working is the same as that previously explained with respect to FIGS. 19 and 20.

It will be observed in FIG. 34 that the unloading station comprising a box 650 with a pivotable bottom 652 is driven by, for instance, an electromagnetic-driven rod 654 which lowers said bottom 652 when a predetermined number of animals are present in box 650. This allows the positioning of a given number of animals in boxes after treatment, which is desirable for directing said animals to appropriate locations.

It can also be foreseen a means for cleaning the surface of table 20 and the vertical part of front piece 50 from the various deposits resulting from the various operations, such as debeaking residues, vaccines, ointments, etc.

Of course, the present invention is by no means limited to the form of embodiment described and illustrated, which have been given by way of example only, but comprises all the means constituting technical equivalents to the means described as well as their combinations, should the latter be performed according to its spirit and carried out within the scope of the following claims. In this respect it is clear that more than one of each treating assembly can be used, for instance more than one debeaking assembly, more than one substance administering assembly (either by drops or spray or injection), more than one powder or ointment applying assembly or more than one cauterizing assembly. The cauterizing assembly can of course be present independently from the presence of the substance administering assembly(ies).

What is claimed is:

1. Apparatus for automatically treating animals such as birds at a high speed, comprising:
a frame,
a spindle mounted on said frame,
drive means for rotating said spindle,
a table mounted on said spindle and provided with a plurality of spaced-apart bird supports, each bird support comprising means for supporting the bird immobilized in the neck area,
movable support means freely mounted on said spindle for moving with respect to said frame from a non-operative position to an operative position,
means for administering a substance to said animals, said means being linked to said movable support means and comprising,
a syringe,
a suction device comprising a perforated nozzle provided with a perforated surface means for surrounding and extending vertically along the neck area retained in the bird support for the purpose of drawing back a predetermined area of the neck skin before an injection is made by said syringe, and
a safety device for preventing administration of the substance when no animal is held in a said bird support, said safety device comprising a feeling member attached to said movable support means and a stop member means for blocking entrance of said feeling member through an opening in said table when no animal is retained in said bird support.

2. The apparatus of claim 1 further comprising a plurality of said syringes and rod means onto which each said syringe is slidingly mounted and to which said suction device is fixed, said rods means being linked to said movable support means.

3. The apparatus of claim 2 wherein said means for administering further comprises syringe support means sliding on said rod means for supporting each said syringe, and articulated lever means for articulation of said syringe support means relative to said movable support means and to said plate.

4. The apparatus of claim 1 further comprising a reservoir, a treating-substance dosage element connected to said reservoir, and a feeding duct connecting said dosage element to said syringe.

5. Apparatus for automatically treating animals such as birds at a high speed, comprising:
a frame,
a spindle mounted on said frame,
drive means for rotating said spindle,
a table mounted on said spindle and provided with a plurality of spaced-apart bird supports, each bird support comprising means for supporting the bird immobilized in the neck area,
movable support means freely mounted on said spindle for moving with respect to said frame from a non-operative position to an operative position,
means for administering a substance to said animals, said means being linked to said movable support means and comprising,
a syringe,
a suction device comprising a perforated nozzle provided with a perforated surface means for surrounding and extending vertically along the neck area retained in the bird support for the purpose of drawing back a predetermined area of the neck skin before an injection is made by said syringe,
a reservoir,
a treating-substance dosage element connected to said reservoir,
a feeding duct connecting said dosage element to said syringe, and
a safety device for preventing administration of the substance when no animal is held in a said bird support said device comprising a feeling member means for passing through said movable support means and having a lower end and an upper end, said upper end having means for actuating said dosage element, and a stop member means for blocking entrance of said lower end through an opening in said table when no bird is retained in said bird support.

* * * * *